(12) United States Patent
Lucas et al.

(10) Patent No.: US 12,296,066 B2
(45) Date of Patent: May 13, 2025

(54) METHODS OF WOUND HEALING WITH SERP-1 POLYPEPTIDES

(71) Applicant: ARIZONA BOARD OF REGENTS ON BEHALF OF ARIZONA STATE UNIVERSITY, Scottsdale, AZ (US)

(72) Inventors: Alexandra Lucas, Tempe, AZ (US); Liqiang Zhang, Chandler, AZ (US); Jordan Yaron, Scottsdale, AZ (US); Grant McFadden, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1028 days.

(21) Appl. No.: 17/056,401

(22) PCT Filed: May 17, 2019

(86) PCT No.: PCT/US2019/032997
§ 371 (c)(1),
(2) Date: Nov. 17, 2020

(87) PCT Pub. No.: WO2019/222710
PCT Pub. Date: Nov. 21, 2019

(65) Prior Publication Data
US 2021/0369910 A1     Dec. 2, 2021

Related U.S. Application Data

(60) Provisional application No. 62/673,386, filed on May 18, 2018.

(51) Int. Cl.
| | | |
|---|---|---|
| *A61K 9/00* | (2006.01) | |
| *A61K 47/36* | (2006.01) | |
| *A61K 47/42* | (2017.01) | |
| *A61L 26/00* | (2006.01) | |
| *A61P 29/00* | (2006.01) | |
| *C07K 14/81* | (2006.01) | |
| *A61K 38/00* | (2006.01) | |

(52) U.S. Cl.
CPC .......... *A61L 26/0066* (2013.01); *A61K 47/36* (2013.01); *A61K 47/42* (2013.01); *A61L 26/008* (2013.01); *C07K 14/8121* (2013.01); *A61K 38/00* (2013.01); *A61L 2300/252* (2013.01)

(58) Field of Classification Search
CPC .............. A61L 26/0066; A61L 26/008; A61L 2300/252; A61K 47/36; A61K 47/42; A61K 38/00; C07K 14/8121
See application file for complete search history.

(56) References Cited

U.S. PATENT DOCUMENTS

2009/0221472 A1* 9/2009 Lucas ..................... A61P 39/06
514/1.1

FOREIGN PATENT DOCUMENTS

WO    WO-2016154041 A1 *  9/2016 ............ A61K 38/07

OTHER PUBLICATIONS

Drumm et al, Genetic Variation and Clinical Heterogeneity in Cystic Fibrosis, Annu. Rev. Pathol. Mech. Dis., 2012, 7, pp. 267-282 (Year: 2012).*
Yampolsky et al, The Exchangeability of Amino Acids in Proteins, Genetics, 2005, 170, pp. 1459-1472. (Year: 2005).*
Nicolaou et al., "Recent Advances in the Chemistry and Biology of Naturally Occurring Antibiotics," Angew Chem Int Ed Engl., 2009, 48(4); 660-719. (Year: 2009).*
UniProt Accession B2CWB4, Serp1 from Myxoma virus, accessed Dec. 2, 2023 at URL rest.uniprot.org/uniprotkb/B2CWB4.txt (Year: 2023).*
Kamoun et al, "A review on polymeric hydrogel membranes for wound dressing applications: PVA-based hydrogel dressings," Journal of Advanced Research 8: 217-233 (published online Feb. 2017) (Year: 2017).*
Kennedy, Controlled Delivery of Serp-1 Protein from Poly(vinyl alcohol) Hydrogel, dissertation, The University of Western Ontario, pp. 1-155 (2010), accessed at https://ir.lib.uwo.ca/cgi/viewcontent.cgi?article=1057&context=etd (Year: 2010).*
Sanchez et al., "Development of Hydrogel with Anti-Inflammatory Properties Permissive for the Growth of Human Adipose Mesenchymal Stem Cells," J. Nanomaterials 2016;2016:8654937, 8 pages (Year: 2016).*
Li et al., "New suitable for tissue reconstruction injectable chitosan/collagen-based hydrogels," Soft Matter 8:3781-3790 (2012) (Year: 2012).*
Wu et al, "Chitosan-Based Composite Hydrogels for Biomedical Applications," Macromol. Res. 25:480-488 (2017) (Year: 2017).*
Mekhail et al, "Injectable Chitosan-Based Scaffolds in Regenerative Medicine and their Clinical Translatability," Advanced Healthcare Materials 3:1529-1545 (2014) (Year: 2014).*
Cui et al, "Development of chitosan-collagen hydrogel incorporated with lysostaphin (CCHL) burn dressing with anti-methicillin-resistant *Staphylococcus aureus* and promotion wound healing properties," Drug Delivery 18:173-180 (2011) (Year: 2011).*
Ambadapadi S, Munuswamy-Ramanujam G, Zheng D, Sullivan C, Dai E, Morshed S, McFadden B, Feldman E, Pinard M, McKenna R, Tibbetts S, Lucas A. Reactive Center Loop (RCL) peptides derived from Serpins display independent coagulation and immune modulating activities. J BiolChem. 2016 (in press).
Borensztajn K., J. Stiekema, S. Nijmeijer, P.H. Reitsma, M.P. Peppelenbosch, C.A. Spek, Factor Xa stimulates proinflammatory and profibrotic responses in fibroblasts via protease-activated receptor-2 activation, Am. J. Pathol. 172 (2008) 309-320. doi:10.2353/ajpath.2008.070347.

(Continued)

*Primary Examiner* — Julie Ha
*Assistant Examiner* — Kristina M Hellman
(74) *Attorney, Agent, or Firm* — BOOTH UDALL FULLER, PLC; Rodney J. Fuller

(57) ABSTRACT

Disclosed herein are topical compositions for treating wounds. The topically compositions include a Serp-1 polypeptide or a nucleic acid encoding a Serp-1 polypeptide. Also disclosed are methods of treating a wound in subject. The methods include administering a topical formulation that includes a Serp-1 polypeptide or a nucleic acid encoding a Serp-1 polypeptide to the wound.

12 Claims, 10 Drawing Sheets

Specification includes a Sequence Listing.

(56) References Cited

OTHER PUBLICATIONS

Brancato, S.K., J.E. Albina, Wound macrophages as key regulators of repair: Origin, phenotype, and function, Am. J. Pathol. 178 (2011) 19-25. doi:10.1016/j.ajpath.2010.08.003.

Chen, H. et al. Myxomavirus-derived serpin prolongs survival and reduces inflammation and hemorrhage in an unrelated lethal mouse viral infection. Antimicrob. Agents Chemother. 57, 4114-4127 (2013).

Dai E. et al., Inhibition of Chemokine-Glycosaminoglycan Interactions in Donor Tissue Reduces Mouse Allograft Vasculopathy and Transplant Rejection, PLoSONE2010 5(5):e10510.

Dai E., H. Guan, L. Liu, S. Little, G. McFadden, S. Vaziri, H. Cao, I.A. Ivanova, L. Bocksch, A. Lucas, Serp-1, a viral anti-inflammatory serpin, regulates cellular serine proteinase and serpin responses to vascular injury, J. Biol. Chem. 278 (2003) 18563-18572. doi:10.1074/jbc.M209683200.

Davis G. E., D.R. Senger, Endothelial extracellular matrix: Biosynthesis, remodeling, and functions during vascular morphogenesis and neovessel stabilization, Circ. Res. (2005). doi:10.1161/01.RES.0000191547.64391.e3.

Dunn L., H.C.G. Prosser, J.T.M. Tan, L.Z. Vanags, M.K.C. Ng, C.A. Bursill, Murine Model of Wound Healing, J. Vis. Exp. (2013) 1-6. doi:10.3791/50265.

Eming, S.A., T. Krieg, J.M. Davidson, Inflammation in wound repair: Molecular and cellular mechanisms, J. Invest. Dermatol. (2007). doi:10.1038/sj.jid.5700701.

Fumakia, M. , E.A. Ho, Nanoparticles encapsulated with LL37 and serpin A1 promotes wound healing and synergistically enhances antibacterial activity, Mol. Pharm. (2016). doi:10.1021/acs.molpharmaceut.6b00099.

Galiano, R.D., J. Michaels V, M. Dobryansky, J.P. Levine, G.C. Gurtner, Quantitative and reproducible murine model of excisional wound healing, Wound Repair Regen. 12 (2004) 485-492. doi:10.1111/j.1067-1927.2004.12404.x.

Hamedi H., S. Moradi, S.M. Hudson, A.E. Tonelli, Chitosan based hydrogels and their applications for drug delivery in wound dressings: A review, Carbohydr. Polym. (2018). doi:10.1016/j.carbpol.2018.06.114.

Hildebrand, A new method for the model-independent assessment of thickness in three-dimensional images, J. Microsc. 185 (1997) 67-75. doi:10.1046/j.1365-2818.1997.1340694.x.

Hoffmann D.C., C. Textoris, F. Oehme, T. Klaassen, A. Goppelt, A. Römer, B. Fugmann, J.M. Davidson, S. Werner, T. Krieg, S.A. Eming, Pivotal role for α1-antichymotrypsin in skin repair, J. Biol. Chem. (2011). doi:10.1074/jbc.M111.249979.

Hsu I., L.M. Parkinson, Y. Shen, A. Toro, T. Brown, H. Zhao, R.C. Bleackley, D.J. Granville, Serpina3n accelerates tissue repair in a diabetic mouse model of delayed wound healing, Cell Death Dis. 5 (2014) e1458-11. doi:10.1038/cddis.2014.423.

Huntington J.A., M. Yamasaki, Serpin polymerization in vitro, Methods Enzymol. (2011). doi:10.1016/B978-0-12-385950-1.00017-1.

Huntington, J. Thromb. Haemost. 9 (2011) 26-34. doi:10.1111/j.1538-7836.2011.04360.x.

Huntington, Structure of a Serpin Polymer and Implications for Conformational Disease, J. Mol. Biol. 293 (1999) 449-455. doi:10.1006/jmbi.1999.3184.

Julier, Z. , A.J. Park, P.S. Briquez, M.M. Martino, Promoting tissue regeneration by modulating the immune system, Acta Biomater. (2017). doi:10.1016/j.actbio.2017.01.056.

Kennedy, "Controlled Delivery of Serp-1 Protein from Poly(vinyl alcohol) Hydrogel", University of Western Ontario Dissertation, (20100800), URL: https://pdfs.semanticscholar.org/dd31/633aae874af26bfe46d14f67ca4146949cae.pdf, (Aug. 1, 2019), XP055655192.

Kotwal G.J. , S. Chien, Macrophage differentiation in normal and accelerated wound healing, in: Results Probl. Cell Differ., 2017. doi:10.1007/978-3-319-54090-0_14.

Lalani et al, The Purified Myxoma Virus Gamma Interferon Receptor Homolog M-T7 Interacts with the Heparin-Binding Domains of Chemokines, j.Virol1997 71(6): 4356-4363.

Landén, N.X., D. Li, M. Ståhle, Transition from inflammation to proliferation: a critical step during wound healing, Cell. Mol. Life Sci. (2016). doi:10.1007/s00018-016-2268-0.

Liu H., C. Wang, C. Li, Y. Qin, Z. Wang, F. Yang, Z. Li, J. Wang, A functional chitosan-based hydrogel as a wound dressing and drug delivery system in the treatment of wound healing, RSC Adv. (2018). doi:10.1039/c7ra13510f.

Liu, X., L. Ma, Z. Mao, C. Gao, Chitosan-based biomaterials for tissue repair and regeneration, Adv. Polym. Sci. (2011). doi:10.1007/12_2011_118.

Lucas A., E. Dai, L. Liu, H. Guan, P. Nash, G. McFadden, L. Miller, Transplant vasculopathy: Viral anti-inflammatory serpin regulation of atherogenesis, J. Hear. Lung Transplant. 19 (2000) 1029-1038. doi:10.1016/S1053-2498(00) 00190-X.

Lucas A., Liu L, Macen J, Nash P, Dai E, Stewart M, Graham K, Etches W, Boshkov L, Nation PN, Humen D, Hobman ML, McFadden G., Virus-Encoded Serine Proteinase Inhibitor SERP-1 Inhibits Atherosclerotic Plaque Development After Balloon Angioplasty Circulation. Dec. 1, 1996;94(11):2890-900.

Mahon, Crystal Structure of Cleaved Serp-1, a Myxomavirus-Derived Immune Modulating Serpin: Structural Design of Serpin Reactive Center Loop Peptides with Improved Therapeutic Function, Biochemistry. 57 (2018) 1096-1107. doi:10.1021/acs.biochem.7b01171.

Miller, L.W., E. Dai, P. Nash, L. Liu, C. Icton, D. Klironomos, L. Fan, P.N. Nation, R. Zhong, G. McFadden, A. Lucas, Inhibition of transplant vasculopathy in a rat aortic allograft model after infusion of anti-inflammatory viral serpin, Circulation. 101 (2000) 1598-1605. doi:10.1161/01.CIR.101.13.1598.

Mohiti-Asli, M., E.G. Loboa, Wound Healing Biomaterials, Wound Heal. Biomater. 1 (2016) 483-499. doi:10.1016/B978-1-78242-456-7.00023-4.

Mossman et al, The Myxoma Virus-soluble Interferon-γ Receptor Homolog, M-T7, Inhibits Interferon-γ in a Species-specific Manner, JBC. 1995 270(7): 3031-3038.

Nussbaum, S.R., M.J. Carter, C.E. Fife, J. DaVanzo, R. Haught, M. Nusgart, D. Cartwright, An Economic Evaluation of the Impact, Cost, and Medicare Policy Implications of Chronic Nonhealing Wounds., Value Health. 21 (2018) 27-32. doi:10.1016/j.jval.2017.07.007.

O'Rourke B.P. , A.H. Kramer, L.L. Cao, M. Inayathullah, H. Guzik, J. Rajadas, J.D. Nosanchuk, D.J. Sharp, Fidgetin-Like 2 siRNA Enhances the Wound Healing Capability of a Surfactant Polymer Dressing, Adv. Wound Care. (2018). doi:10.1089/wound.2018.0827.

Osman, A novel method to assess collagen architecture in skin, BMC Bioinformatics. 14 (2013) 1. doi:10.1186/1471-2105-14-260.

Pereira, R.F., P.J. Bártolo, Traditional Therapies for Skin Wound Healing, Adv. Wound Care. (2016). doi:10.1089/wound.2013.0506.

Rao, J., C. Zhao, A. Zhang, H. Duan, P. Hao, R.-H. Wei, J. Shang, W. Zhao, Z. Liu, J. Yu, K.S. Fan, Z. Tian, Q. He, W. Song, Z. Yang, Y.E. Sun, X. Li, NT3-chitosan enables de novo regeneration and functional recovery in monkeys after spinal cord injury, Proc. Natl. Acad. Sci. (2018). doi:10.1073/pnas.1804735115.

Riva, R. , H. Ragelle, A. Des Rieux, N. Duhem, C. Jérôme, V. Préat, Chitosan and chitosan derivatives in drug delivery and tissue engineering, Adv. Polym. Sci. (2011). doi:10.1007/12_2011_137.

Roszer, T., Understanding the mysterious M2 macrophage through activation markers and effector mechanisms, Mediators Inflamm. (2015). doi:10.1155/2015/816460.

Ruifrok and Johnston, Quantification of histochemial staining by color deconvolution, (Ruifrok, Anal. Quant. Cytol. Histol. 23 (2001) 291-9.

Saito, New Algorithms for Euclidean Distance Transformation of an n-Dimentionsl Digitized Picture with Applications, Pattern Recognit. 27 (1994) 1551-1565. doi:10.1016/0031-3203(94)90133-3).

Schindelin J., I. Arganda-Carreras, E. Frise, V. Kaynig, M. Longair, T. Pietzsch, S. Preibisch, C. Rueden, S. Saalfeld, B. Schmid, J.-Y. Tinevez, D.J. White, V. Hartenstein, K. Eliceiri, P. Tomancak, A. Cardona, Fiji: an open-source platform for biological-image analysis, Nat. Methods. 9 (2012) 676-682. doi:10.1038/nmeth.2019.

(56) References Cited

OTHER PUBLICATIONS

Sen C.K., G.M. Gordillo, S. Roy, R. Kirsner, L. Lambert, T.K. Hunt, F. Gottrup, G.C. Gurtner, M.T. Longaker, "Human skin wounds: a major and snowballing threat to public health and the economy.," Wound Repair Regen. 17 (2009) 763-71. doi:10.1111/j.1524-475X.2009.00543.x.

Sensini, "Biofabrication of bundles of poly(lactic acid)-collagen blends mimicking the fascicles of the human Achille tendon," Biofabrication. 9 (2017) 015025. doi:10.1088/1758-5090/aa6204.

Shen, Y., M.R. Zeglinski, C.T. Turner, S.A. Raithatha, Z. Wu, V. Russo, C. Oram, S. Hiroyasu, L. Nabai, H. Zhao, T. Bozin, K. Westendorf, I. Kopko, R. Huang, S. Arns, J. Tan, H. Zeng, A. Boey, R. Liggins, J. Jaquith, D.R. Cameron, A. Papp, D.J. Granville, "Topical small molecule granzyme B inhibitor improves remodeling in a murine model of impaired burn wound healing," Exp. Mol. Med. (2018). doi:10.1038/s12276-018-0095-0.

Simone, T.M., C.E. Higgins, R.-P. Czekay, B.K. Law, S.P. Higgins, J. Archambeault, S.M. Kutz, P.J. Higgins, "SERPINE1: A Molecular Switch in the Proliferation-Migration Dichotomy in Wound—"Activated" Keratinocytes," Adv. Wound Care. 3 (2014) 281-290. doi:10.1089/wound.2013.0512.

Singer et al., Healing, Cutaneous Wound Healing, N. Engl. J. Med. (1999) 738. doi:10.1056/NEJM199909023411006.

Stejskalová and Almquist, "Using biomaterials to rewire the process of wound repair," Biomater. Sci. 5 (2017) 1421-1434. doi:10.1039/C7BM00295E.

Tardif, J.-C. et al. "A randomized controlled, phase 2 trial of the viral serpin Serp-1 in patients with acute coronary syndromes undergoing percutaneous coronary intervention." Circ. Cardiovasc. Interv. 3, 543-8 (2010).

Tonnesen, V, X. Feng, R.A.F. Clark, "Angiogenesis in wound healing," J. Investig. Dermatology Symp. Proc. (2000). doi:10.1046/j.1087-0024.2000.00014.x.

Upton C. et al., "Encoding of a Homolog of the IFN-y Receptor by Myxoma Virus," Science. 1992 258(5086) 1369-1372.

Upton, Z., et al., "Growth factor complexes hold potential as a wound therapy approach," J. Invest. Dermatol. 128 (2008) 1535-1544. doi:10.1038/sj.jid.5701148.

Vanchinathan, V., et al., "The vascular marker CD31 also highlights histiocytes and histiocyte-like cells within cutaneous tumors," Am. J. Clin. Pathol. (2015). doi:10.1309/AJCPRHM8CZH5EMFD.

Veith A. P., et al., Therapeutic strategies for enhancing angiogenesis in wound healing., Adv. Drug Deliv. Rev. (2018). doi:10.1016/j.addr.2018.09.010.

Vermonden, T., R. Censi, W.E. Hennink, "Hydrogels for Protein Delivery," Chem. Rev. (2012). doi:10.1021/cr200157d.

Wang, J., "Neutrophils in tissue injury and repair," Cell Tissue Res. (2018). doi:10.1007/s00441-17-2785-7.

Wang, X., et al., "The mouse excisional wound splinting model, including applications for stem cell transplantation," Nat. Protoc. 8 (2013) 302-309. doi:10.1038/nprot.2013.002.

Wynn, T.A., K.M. Vannella, "Macrophages in Tissue Repair, Regeneration, and Fibrosis," Immunity. 44 (2016) 450-462. doi:10.1016/j.immuni.2016.02.015.

Yang, Z., et al., "NT3-chitosan elicits robust endogenous neurogenesis to enable functional recovery after spinal cord injury," Proc. Natl. Acad. Sci. (2015). doi:10.1073/pnas.1510194112.

Zhang, et al., "A systematic and quantitative methof for wound-dressing evaluation," Burn. Trauma. 3 (2015) 1-8. doi:10.1186/s41038-015-0013-9.

Zhao, R., et al., "Inflammation in chronic wounds," Int. J. Mol. Sci. (2016). doi:10.3390/ijms17122085.

\* cited by examiner

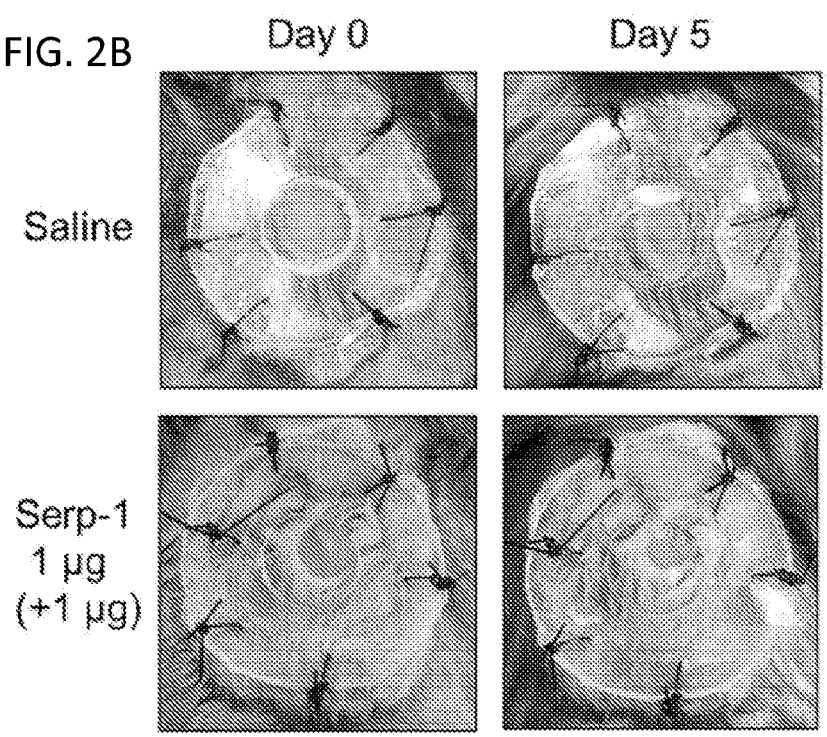

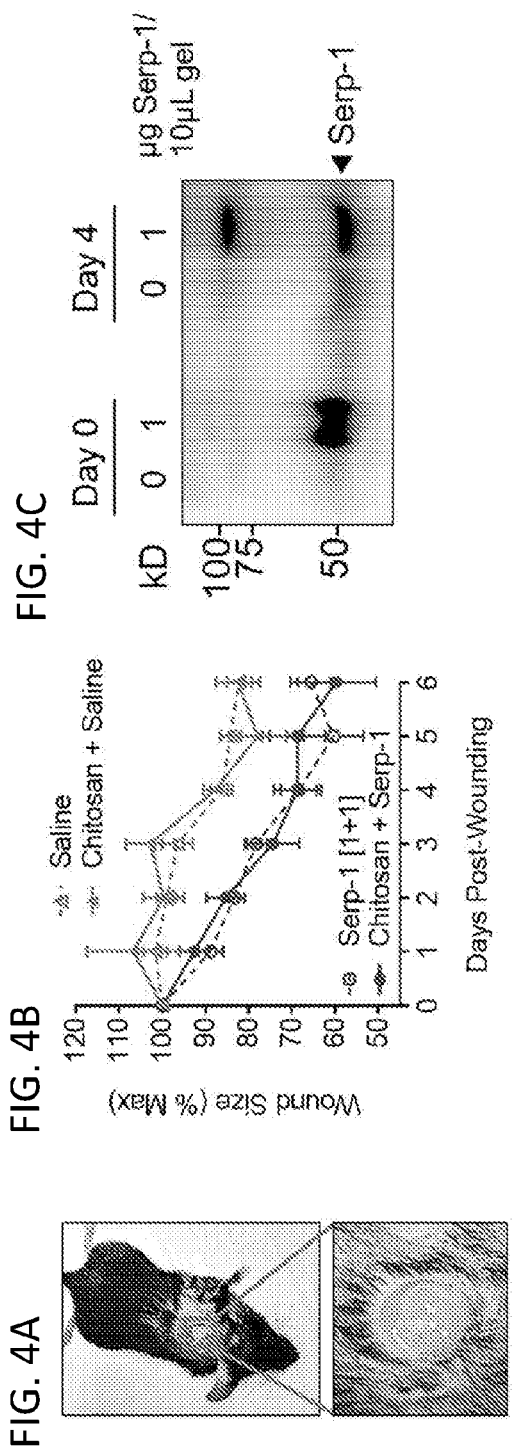

FIG. 6A
FIG. 6B
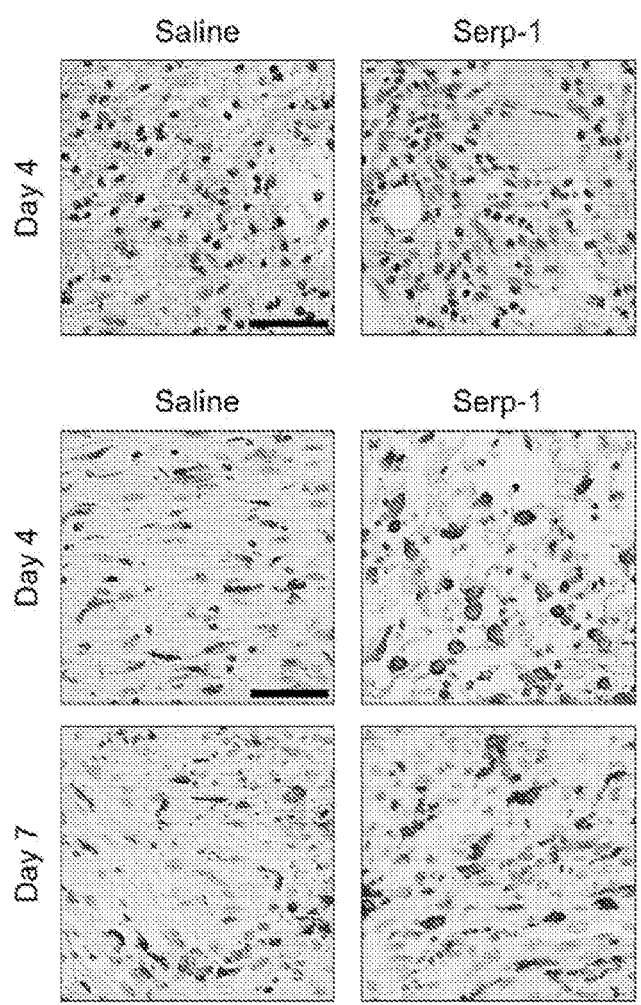
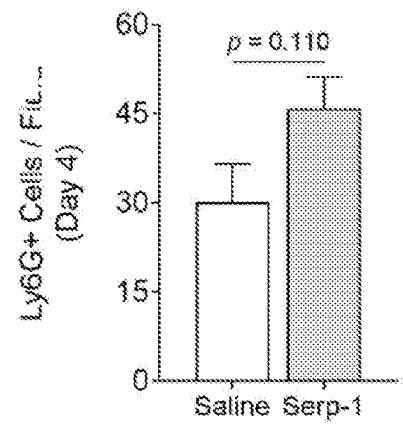
FIG. 6C
FIG. 6D

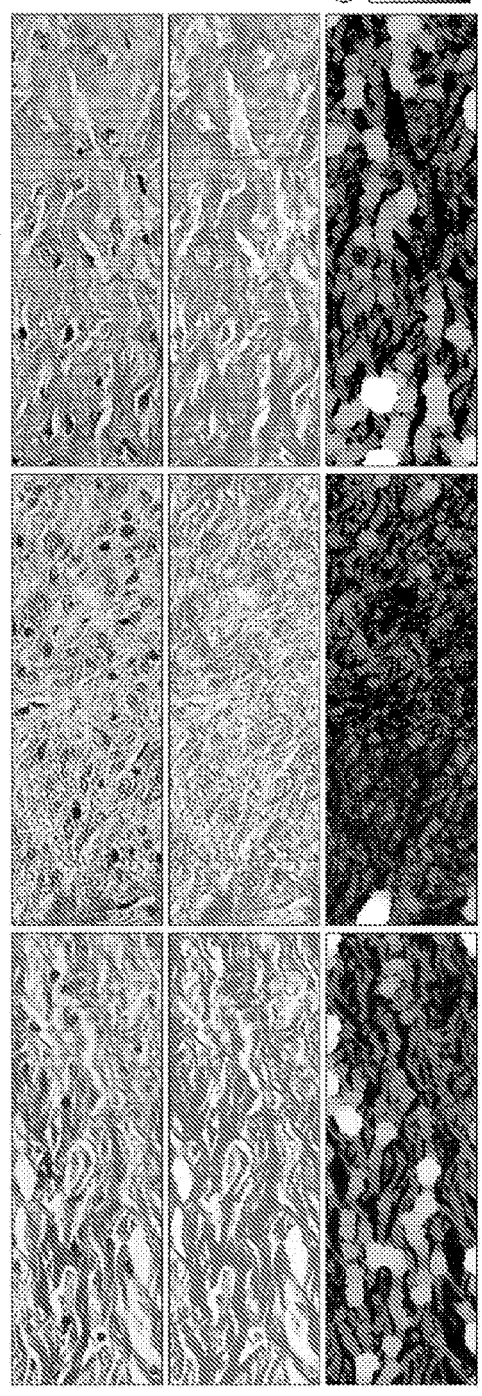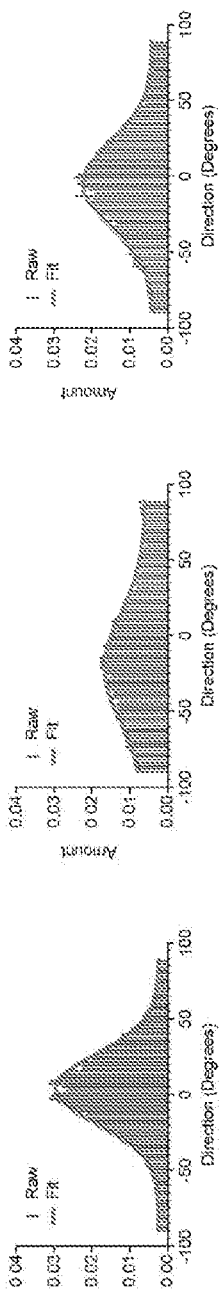
FIG. 7A
FIG. 7B
FIG. 7C
FIG. 7D

SEQUENCE LISTING

<160> NUMBER OF SEQ ID NOS: 5

<210> SEQ ID NO 1
<211> LENGTH: 350
<212> TYPE: PRT
<213> ORGANISM: Homo sapiens

<400> SEQUENCE: 1

Met Lys Tyr Leu Val Leu Val Leu Cys Leu Thr Ser Cys Ala Cys Arg
1               5                   10                  15

Asp Ile Gly Leu Trp Thr Phe Arg Tyr Val Tyr Asn Glu Ser Asp Asn
            20                  25                  30

Val Val Phe Ser Pro Tyr Gly Leu Thr Ser Ala Leu Ser Val Leu Arg
        35                  40                  45

Ile Ala Ala Gly Gly Asn Thr Lys Arg Glu Ile Asp Val Pro Glu Ser
    50                  55                  60

Val Val Glu Asp Ser Asp Ala Phe Leu Ala Leu Arg Glu Leu Phe Val
65                  70                  75                  80

Asp Ala Ser Val Pro Leu Arg Pro Glu Phe Thr Ala Glu Phe Ser Ser
                85                  90                  95

Arg Phe Asn Thr Ser Val Gln Arg Val Thr Phe Asn Ser Glu Asn Val
            100                 105                 110

Lys Asp Val Ile Asn Ser Tyr Val Lys Asp Lys Thr Gly Gly Asp Val
        115                 120                 125

Pro Arg Val Leu Asp Ala Ser Leu Asp Arg Asp Thr Lys Met Leu Leu
    130                 135                 140

Leu Ser Ser Val Arg Met Lys Thr Ser Trp Arg His Val Phe Asp Pro
145                 150                 155                 160

Ser Phe Thr Thr Asp Gln Pro Phe Tyr Ser Gly Asn Val Thr Tyr Lys
                165                 170                 175

Val Arg Met Met Asn Lys Ile Asp Thr Leu Lys Thr Glu Thr Phe Thr
            180                 185                 190

Leu Arg Asn Val Gly Tyr Ser Val Thr Glu Leu Pro Tyr Lys Arg Arg
        195                 200                 205

Gln Thr Ala Met Leu Leu Val Val Pro Asp Asp Leu Gly Glu Ile Val
    210                 215                 220

Arg Ala Leu Asp Leu Ser Leu Val Arg Phe Trp Ile Arg Asn Met Arg
225                 230                 235                 240

Lys Asp Val Cys Gln Val Val Met Pro Lys Phe Ser Val Glu Ser Val
                245                 250                 255

Leu Asp Leu Arg Asp Ala Leu Gln Arg Leu Gly Val Arg Asp Ala Phe
            260                 265                 270

Asp Pro Ser Arg Ala Asp Phe Gly Gln Ala Ser Pro Ser Asn Asp Leu
        275                 280                 285

Tyr Val Thr Lys Val Leu Gln Thr Ser Lys Ile Glu Ala Asp Glu Arg
    290                 295                 300

Gly Thr Thr Ala Ser Ser Asp Thr Ala Ile Thr Leu Ile Pro Arg Asn
305                 310                 315                 320

Ala Leu Thr Ala Ile Val Ala Asn Lys Pro Phe Met Phe Leu Ile Tyr
                325                 330                 335

His Lys Pro Thr Thr Thr Val Leu Phe Met Gly Thr Ile Thr
            340                 345                 350

<210> SEQ ID NO 2
<211> LENGTH: 6

-continued

```
<212> TYPE: PRT
<213> ORGANISM: Homo sapiens

<400> SEQUENCE: 2

Ile Pro Arg Asn Ala Leu
1               5

<210> SEQ ID NO 3
<211> LENGTH: 4
<212> TYPE: PRT
<213> ORGANISM: Homo sapiens

<400> SEQUENCE: 3

Arg Asn Ala Leu
1

<210> SEQ ID NO 4
<211> LENGTH: 8
<212> TYPE: PRT
<213> ORGANISM: Homo sapiens

<400> SEQUENCE: 4

Thr Ala Ile Val Ala Asn Lys Pro
1               5

<210> SEQ ID NO 5
<211> LENGTH: 15
<212> TYPE: PRT
<213> ORGANISM: Homo sapiens

<400> SEQUENCE: 5

Gly Thr Thr Ala Ser Ser Asp Thr Ala Ile Thr Leu Ile Pro Arg
1               5                   10                  15
```

METHODS OF WOUND HEALING WITH SERP-1 POLYPEPTIDES

CROSS REFERENCE TO RELATED APPLICATIONS

This application is a 371 U.S. national stage application of PCT/US2019/032997, filed on May 17, 2019, which claims the benefit of the earlier filing date of U.S. Provisional Application No. 62/673,386, filed May 18, 2018. Each of these applications is specifically incorporated by reference herein in its entirety.

STATEMENT OF GOVERNMENT SUPPORT

This invention was made with government support under RC1HL100202 awarded by National Institutes of Health. The government has certain rights in the invention.

TECHNICAL FIELD

This disclosure resides in the field of wound healing compositions and use thereof. Particularly, this disclosure relates to compositions of Serp-1 and its derivatives, including active fragments thereof and the topical application of these compositions to skin wounds to expedite the wound healing process.

BACKGROUND

Wounds (i.e., lacerations or openings) in mammalian tissue result in tissue disruption and coagulation of the microvasculature at the wound face. Wound healing is a process by which these wounds on the skin of a subject heal and eventually close. Repair of such tissue represents an orderly, controlled cellular response to injury. All soft tissue wounds, regardless of size, heal in a similar manner. Tissue regrowth and repair are biologic systems wherein cellular proliferation and angiogenesis occur in the presence of an oxygen gradient. The sequential morphological and structural changes which occur during tissue repair have been characterized in great detail and have in some instances been quantified. When the injured surface is large, becomes infected, or in patients with poor healing capacity such as diabetics or the elderly or bedridden patients, then wound healing can be prolonged and lead to chronic ulceration and further complications with even limb loss or increased morbidity and mortality. Thus, there is a need for improved wound management.

BRIEF DESCRIPTION OF THE DRAWINGS

FIGS. 2A-2B show that Serp-1 dose- and schedule-dependently accelerates full-thickness wound healing in mice. FIG. 2A is a set of digital images showing an overview of the surgical method for creating the full-thickness splinted wound healing model: 1,2) A punch biopsy injury is performed on the dorsal, interscapular skin of an anesthetized mouse; 3) Serp-1 treatment or saline control is delivered directly to the wound bed; 4) a silicone splint overlaid with Tegaderm is applied to the back with a thin layer of cyanoacrylate glue; 5) the silicone splint is sutured to the back of the mouse; 6) the wound is photographed and the mouse is monitored until recovered. FIG. 2B is a set of digital images of representative examples of Day 0 and Day 5 wounds of mice treated with saline alone (top panels) or Serp-1 as a 1 µg/mouse dose on both Day 0 and Day 3 post-wounding.

FIG. 3A is the molecular structure of chitosan polymer (top) and a digital image of a chitosan-collagen hydrogel (bottom). FIG. 3B is a digital image of a scanning electron microscope imaging at 15,000 magnification of chitosan-collagen hydrogel illustrates the complex high surface area facilitating binding of therapeutic proteins. FIG. 3C is a digital image of an immunoblot demonstrating dose-dependent release of Serp-1 from the chitosan-collagen hydrogel into PBS over a period of 4 days. Arrow indicates monomeric Serp-1, high molecular weight band represents Serp-1 dimers.

FIGS. 4A-4C show the application of chitosan-collagen hydrogel containing Serp-1 can efficiently promote wound healing on mouse model. FIG. 4A is digital images of a representative mouse with full-thickness wound treated with chitosan-collagen hydrogel (zoom). FIG. 4B is a graph showing a time-course demonstrating that saline alone and chitosan-collagen hydrogel loaded with saline and Serp-1 [1+1] and chitosan-collagen hydrogel loaded with Serp-1 have identical wound healing kinetics. FIG. 4C is a digital image of an immunoblot showing release of Serp-1 (arrow) from chitosan-collagen hydrogels at Day 0 and Day 4 directly from the wound beds of mice. High molecular weight band indicates Serp-1 dimer.

FIG. 5A are representative digital images of immunohistochemistry of wounds at day 7 probed with anti-CD31 antibody. Arrows indicate CD31+ endothelial cells in peri-wound blood vessels. Dotted blue line indicates the wound boundary, with the wound bed to the left of the line. FIG. 5B is a bar graph showing the quantification of CD31-positive vessels at Day 7 in the peri-wound area of mice treated with saline or Serp-1. Bars represent mean±standard error. Statistics were calculated by Student's T-test.

FIGS. 6A-6D show that Serp-1 stimulates enhanced anti-inflammatory immune response in wounds. FIG. 6A is a set of digital images of representative immunohistochemistry images of Ly6G staining in 4 day old wounds of mice treated with saline or Serp-1. FIG. 6B is a graph showing quantification of Ly6G+ cells (representative of peripheral granulocytes). FIG. 6C is a set of digital images of representative immunohistochemistry images of Ly6G staining in 4 and 7 day old wounds of mice treated with saline or Serp-1. FIG. 6D is a graph showing quantification of Ly6G+ cells (representative of peripheral granulocytes).

FIGS. 7A-7D show quantitative collagen texture analysis. FIG. 7A is a digital image of representative 20× images of normal (left), saline treated (middle) and Serp-1 treated (right) skin stained with Masson's Trichrome. FIG. 7B is a digital image of deconvolution of the blue-stained connective tissue component of the trichrome staining. FIG. 7C is a digital image showing local thickness analysis with heat-mapped visualization (more purple/black=less thick; more yellow/white=more thick). FIG. 7D is a set of graphs showing raw and fit data of directionality of the collagen component of the trichrome stain. Greater peaks in the data indicate more preference for a single direction by the component of the image, while a more flat distribution indicates less directionality or preference for a single direction.

DETAILED DESCRIPTION OF SEVERAL EMBODIMENTS

Figure 1A:
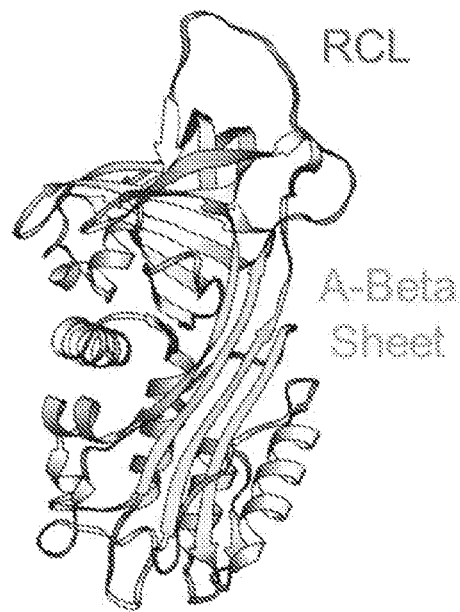
FIG. 1A shows the structure of Serp-1 depicting a classic serpin structure with reactive center loop (RCL) and A-Beta sheet.

This technology disclosed herein is described in one or more exemplary embodiments in the following description with reference to the Figures. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" means "includes." Hence "comprising A or B" means including A, B, or A and B. It is further to be understood that all base sizes and all molecular weight or molecular mass values given for peptides and nucleic acids are approximate and are provided for description.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, rodents (e.g., mice, rats, etc.) and the like. Preferably, the subject is a human patient. In particular embodiments, the subject of this disclosure is a human subject. A "subject in need thereof" or "a subject in need of" is a subject known to have, or is suspected of having a surface wound, such as a wound in the skin and surrounding tissue.

As used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

A "hydrogel" is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, chitosan, polyphosphazenes, and polyacrylates such as poly-hydroxyethyl methacrylate (poly-HEMA) and poly-N-(2-hydroxypropyl) methacrylamide (poly-HPMA), which are cross-linked ionically, or block copolymers such as PLURONICS™ (BASF Corporation) or TETRONICS™ (BASF Corporation), polyethylene oxide-polypropylene glycol block copolymers which are crosslinked by temperature or pH sensing probes, respectively. Other materials include proteins such as fibrin, polymers such as polyvinylpyrrolidone, hyaluronic acid and collagen.

A "peptide", "polypeptide", and/or protein: Any compound composed of amino acids, amino acid analogs, chemically bound together. Amino acids generally are chemically bound together via amide linkages (CONH). Additionally, amino acids may be bound together by other chemical bonds. For example, the amino acids may be bound by amine linkages. Peptides include oligomers of amino acids, amino acid analog, or small and large peptides, including polypeptides or proteins.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Although methods and materials similar or equivalent to those described herein can be used in the practice or testing of the present disclosure, suitable methods and materials are described below. All publications, patent applications, patents, and other references mentioned herein are incorporated by reference in their entirety. Unless otherwise defined, all technical terms used herein have the same meaning as commonly understood. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999. In addition, the materials, methods, and examples are illustrative only and not intended to be limiting.

INTRODUCTION

Large surface wounds, including lacerations and burns, are common and often complex injuries. In some cases, comorbidities such as diabetes and advanced age cause skin lesions to turn into non-healing chronic wounds, reducing function and increasing risk of infection and bleeding. Chronic non-healing wounds can be life threatening and are a major threat to public health and a large cost to the economy (Sen et al., Wound Repair Regen. 17 (2009) 763-71. doi: 10.1111/j.1524-475X.2009.00543.x, Nussbaum et al., Value Health. 21 (2018) 27-32. doi: 10.1016/j.jval.2017.07.007). According to the NIH ARRA Impact Report, over 6 million cases of chronic wounds occur annually in the United States with a collective cost of more than $20 billion per year. Severe burn injuries cause about 40,000 hospitalizations and nearly 4,000 deaths each year. Notably, these numbers do not include scar revisions, which amount to over 170,000 procedures annually in the U.S.A (Lim et al., Plast. Reconstr. Surg. 133 (2014) 398-405. doi: 10.1097/01.prs.0000436526.64046.d0).

The wound healing process is frequently divided into three steps: hemostasis and inflammation, new tissue generation and remodeling (Eming et al., Sci. Transl. Med. 6 (2014). doi:10.1126/scitranslmed.3009337), where the immune system plays a central role in each step. Wound healing in adults commonly begins with bleeding and clot formation (haemostasis) followed by a rapid-onset of inflammation. Immune response cells, including neutrophils (Wilgus et al., Adv. Wound Care. (2013). doi:10.1089/wound.2012.0383, Soehnlein et al., Nat. Rev. Immunol. (2017). doi:10.1038/nri.2017.10) and macrophages (Lucas et al., J. Immunol. 184 (2010) 3964-3977. doi:10.4049/jimmunol.0903356, Hesketh et al., Int. J. Mol. Sci. (2017). doi:10.3390/ijms18071545, Wynn and Vannella, Immunity. 44 (2016) 450-462. doi:10.1016/j.immuni.2016.02.015, Mantovani et al., J. Pathol. (2013). doi:10.1002/path.4133, Brancato and AlbinaAm. J. Pathol. 178 (2011) 19-25. doi: 10.1016/j.ajpath.2010.08.003) are known to be crucial in initiating the early stage of wound healing. The serine proteases in the coagulation and fibrinolytic cascades that regulate clotting and bleeding are also known to closely interact with cells that regulate inflammation. Thus, the serine proteases and inflammatory response cells collaborate in early stages of wound healing. Acute inflammation is critical to healthy wound healing, with innate immunity driving early responses to injury and with precisely regulated stages at both the cellular and molecular levels, while sustained and excessive inflammation can exacerbate damage and result in chronic wounds (Eming et al., J. Invest. Dermatol. (2007). doi:10.1038/sj.jid.5700701, Landén et al., Cell. Mol. Life Sci. (2016). doi:10.1007/s00018-016-2268-0).

It has been widely recognized that modulating the immune system through biomaterials and drug delivery systems can alter wound healing, increasing regeneration and reducing fibrosis (Zhao et al., Int. J. Mol. Sci. (2016). doi:10.3390/ijms17122085, Julier et al., Acta Biomater. (2017). doi:10.1016/j.actbio.2017.01.056, Stejskalová and Almquist, Biomater. Sci. 5 (2017) 1421-1434. doi:10.1039/C7BM00295E). The three major factors that are known to fundamentally alter wound healing and management are infection, wound closure and fibrosis (scarring). Accordingly, attention has been directed towards technologies that inhibit infection, promote wound closure, and reduce scarring, either individually or simultaneously.

Serine protease inhibitors, or serpins, are ubiquitous, complex, and highly active regulatory molecules that effectively control multiple coagulation, inflammatory, and neuroendocrine pathways. Mechanistically, Serp-1 inhibits plasminogen activators, tPA and uPA, and complexes with uPAR, actin binding protein filamin B and vitronectin. Serp-1 also binds and inhibits clotting factors X and thrombin providing a balanced effect of the pro-thrombotic and pro-thrombolytic cascades, thus reducing risk of bleeding, or conversely, excess clotting. Interestingly, all of these factors are also involved in wound healing, where they play central roles in modulating inflammation, cell migration, wound closure, tissue remodeling and fibrosis (Simone et al., Adv. Wound Care. 3 (2014) 281-290. doi:10.1089/wound.2013.0512; Upton, et al., J. Invest. Dermatol. 128 (2008) 1535-1544. doi:10.1038/sj.jid.5701148, Borensztajn et al., Am. J. Pathol. 172 (2008) 309-320. doi:10.2353/ajpath.2008.070347). Serp-1, is a secreted glycoprotein derived from Myxomavirus that interferes with the host inflammatory response, e.g. innate immune responses to infection in the European rabbit (*Oryctolagus cuniculus*). Serp-1 has a typical SERPIN structure with reactive center loop-RCL and β-sheets (FIG. 1A), As disclosed herein the inventors have discovered that topical compositions that include Serp-1 polypeptides, for example full length Serp-1 polypeptide or biologically active fragments thereof improve the rate of healing as compared to wounds that have not been treated with Serp-1. This novel topical therapeutic approach improves the rate of wound healing. It was shown that Serp-1 at doses of between 1 microgram and 2 micrograms used as a topical application to punch wounds on the mouse back, accelerated the time to wound closure by 2-5 days with topical treatment when compared to saline. Further improvement was also seen with 1 microgram doses followed by a second bolus given at 3 days.

Compositions

Disclosed herein topical formulations that include Serp-1 polypeptides and/or biologically active fragments and derivatives thereof, for example, Serp-1 polypeptides and fragments thereof that promote wound healing in a mammalian subject topically administered a Serp-1 polypeptide or a fragment thereof. In certain embodiments, a topical formulation includes an effective amount, such as a therapeutically effective amount of a Serp-1 polypeptide. In certain embodiments, an effective amount is between about 0.1 µg and 3 µg, such as 0.1 µg, 0.2 µg, 0.3 µg, 0.4 µg, 0.5 µg, 0.6 µg, 0.7 µg, 0.8 µg, 0.9 µg, 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, or 3.0 µg. In certain embodiments, a Serp-1 polypeptide has been modified so that splice sites are removed. In one embodiments, a Serp-1 polypeptide comprises the amino acid available at GENBANK accession no. NP_051722 and having the amino acid sequence set forth as:
MKYLVLVLCL TSCACRDIGL WTFRYVYNES DNVVFSPYGL TSALSVLRIA AGGNTKREID VPESVVEDSD AFLALRELFV DASVPLRPEF TAEFSSRFNT SVQRVTFNSE NVKDVINSYV KDKTGGDVPR VLDASLDRDT KMLLLSSVRM KTSWRHVFDP SFTTDQPFYS GNVTYKVRMM NKIDTLKTET FTLRNVGYSV TELPYKRRQT AMLL-VVPDDL GEIVRALDLS LVRFWIRNMR KDVCQVVMPK FSVESVLDLR DALQRLGVRD AFDPSRADFG QASPSNDLYV TKVLQTSKIE ADERGTTASS DTAITLIPRN ALTAIVANKP FMFLIYHKPT TTVLFMGTIT (SEQ ID NO: 1. Serp-1 polypeptides includes polypeptides having at least 80%, such as at least 81%, at least 82%, at least 83%, at least 84%, at least 85%, at least 86%, at least 87%, at least 88%, or at least 89% at least 90%, at least 91%, at least 92%, at least 93%, at least 94%, at least 95%, at least 96%, at least 97%, at least 98%, at least 99% or even 100% sequence identity to the amino acid sequence set forth as SEQ ID NO: 1 as well as biologically active fragments thereof. In embodiments, a Serp-1 polypeptide includes a Serp-1 reactive center loop-derived peptide or a series of modified RCL peptides. In some embodiments, Serp-1 reactive center loop-derived peptide has an amino acid at least 95%, at least 96%, at least 97%, at least 98%, at least 99% or even 100% sequence identity to the amino acid sequence set forth as one of IPRNAL (SEQ ID NO: 2); RNAL (SEQ ID NO: 3); TAIVANKPF (SEQ ID NO: 4); or GTTASSDTAITLIPR (SEQ ID NO: 5).

The disclosed isolated peptides include synthetic embodiments of peptides described herein. In addition, analogs (non-peptide organic molecules), derivatives (chemically functionalized peptide molecules obtained starting with the disclosed peptide sequences) and variants (homologs) of these peptides can be utilized in the compositions ans methods described herein. Each peptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. In another example, carboxylic acid groups of the protein, whether carboxyl-terminal or side chain, can be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to C1-C16 alkyl or dialkyl amino or further converted to an amide.

Hydroxyl groups of the peptide side chains may be converted to C1-C16 alkoxy or to a C1-C16 ester using well-recognized techniques. Phenyl and phenolic rings of the peptide side chains may be substituted with one or more halogen atoms, such as fluorine, chlorine, bromine or iodine, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides to select and provide conformational constraints to the structure that result in enhanced stability. While the peptides of the present disclosure can be linear or cyclic, cyclic peptides generally have an advantage over linear peptides in that their cyclic structure is more rigid and hence their biological activity can be higher than that of the corresponding linear peptide. Any method for cyclizing peptides can be applied to the serpin-derived peptides or fragments described herein.

As noted, the Serp-1 polypeptides can vary in length and can be or can include contiguous amino acid residues that naturally occur in Serp-1 or that vary to a certain degree from a naturally occurring Serp-1 sequence (but retain a biological activity). Where the fragments include, at their N-terminus or C-terminus (or both), amino acid residues that are not naturally found in Serp-1 the additional sequence(s) can be about 200 amino acid residues long, and these residues can be divided evenly or unevenly between the N- and C-termini. For example, both the N- and C-termini can include about 10, 20, 30, 40, 50, 60, 70, 80, 90, or 100 amino acid residues. Alternatively, one terminus can include about 10, 20, 30, 40, 50, 60, 70, 80, 90, 100, 110, 120, 130, 140, 150, 160, 170, 180, 190, or 200 residues, and one terminus can include none (e.g., it can terminate in an amino acid sequence identical to a naturally occurring Serp-1 sequence).

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues. Where biologically active variants of a Serp-1 fragment are used, the variant can vary by substitution of one or more amino acid residues within these groups. The variants can include a conservative amino acid substitution.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a peptide having measurable Serp-1 activity. For computer modeling applications, a pharmacophore is an idealized three-dimensional definition of the structural requirements for biological activity. Peptido- and organomimetics can be designed to fit each pharmacophore with current computer modeling software.

In embodiments, a Serp-1 polypeptide is included in a fusion protein. Thus, the fusion protein can include a Serp-1 polypeptide and a second heterologous moiety, such as a myc protein, an enzyme or a carrier (such as a hepatitis carrier protein or bovine serum albumin) covalently linked to the Serp-1 polypeptide. A second heterologous moiety can be covalently or non-covalently linked to the Serp-1 polypeptide. The Serp-1 polypeptide can be included in a fusion protein and can also include heterologous sequences.

Nucleic acids encoding one or more Serp-1 polypeptide are envisioned. These polynucleotides include DNA, cDNA and RNA sequences which encode the peptide(s) of interest. Nucleic acid molecules encoding these peptides can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same peptide.

Nucleic acid sequences encoding one or more Serp-1 polypeptide can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68: 109-151, 1979; the diethylphosphoramidite method of Beaucage et al., Tetra. Lett. 22: 1859-1862, 1981 the solid phase phosphoramidite triester method described by Beaucage & Caruthers, Tetra. Letts. 22(20): 1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding one or more Serp-1 polypeptide disclosed herein can be prepared by cloning techniques or chemical synthesis. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (San Diego, CA), and Applied Biosystems (Foster City, CA), as well as many other commercial sources known to one of skill.

Once the nucleic acids encoding one or more Serp-1 polypeptide are isolated and cloned, the peptide can be expressed in a recombinantly engineered cell such as bacteria, plant, yeast, insect and mammalian cells using a suitable expression vector or expressed in a viral vector for therapeutic approaches—eg Adeno-associated viral (AAV) vector expression. One or more DNA sequences encoding one or more immunogenic peptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. In one example a vector is an adeno-associated virus (AAV) vectror.

Polynucleotide sequences encoding one or more Serp-1 polypeptide can be operatively linked to expression control sequences (e.g., a promoter). An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding one or more Serp-1 polypeptide can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

In an aspect, a composition disclosed herein comprises nucleic acid molecules that encode the serpin-derived peptides or fragments thereof disclosed herein in an expression construct or in a single or separate cassette. Disclosed herein is an expression construct capable of expressing serpin-derived peptides or fragments thereof.

A disclosed expression cassette can include 5' and 3' regulatory sequences operably linked to a polynucleotide disclosed herein. "Operably linked" is intended to mean a functional linkage between two or more elements. For example, an operable linkage between a polynucleotide disclosed herein and a regulatory sequence (e.g., a promoter) is a functional link that allows for expression of a polynucleotide disclosed herein. Operably linked elements can be contiguous or non-contiguous. When used to refer to the joining of two protein coding regions, by operably linked is intended that the coding regions are in the same reading frame. An expression cassette may further comprise at least one additional polynucleotide to be co-transformed into the organism. Alternatively, one or more polypeptide(s) can be expressed on one or more expression cassettes. Expression cassettes can be provided with a plurality of restriction sites and/or recombination sites for insertion of the polynucleotide to be under the transcriptional regulation of the regulatory regions.

The regulatory regions (i.e., promoters, transcriptional regulatory regions, and translational termination regions) and/or the polynucleotides disclosed herein can be native/analogous to the host cell or to each other. Alternatively, the regulatory regions and/or the polynucleotide employed in the invention can be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction, annealing, resubstitutions, e.g., transitions and transversions, can be involved.

A number of promoters can be used in the practice of the invention. The promoters can be selected based on the desired outcome. The choice of promoters depends on several factors including but not limited to efficiency, selectability, inducibility, desired expression level, and cell- or tissue-preferential expression. The nucleic acids can be combined with constitutive, tissue-preferred, inducible, or other promoters for expression in the host organism. One skilled in the art is capable of appropriately selecting and positioning promoters and other regulator}' regions relative to the coding sequence.

In addition to Serp-1 polypeptide and/or nucleic acids encoding the Serp-1 polypeptides, the topical formulation can further comprises one or more carriers and excipients, including viscosity increasing agents, ointment bases (e.g., cream bases), antimicrobial preservatives, temperature and pH sensing probes, emulsifying agents, and/or solvents.

A "viscosity increasing agent" is an agent that is used to thicken a formulation. Exemplary viscosity increasing agents may include, for example, cetostearyl alcohol, cholesterol, stearyl alcohol, chlorocresol, white wax, stearic acid, cetyl alcohol, or a combination thereof. The viscosity increasing agent may be present in the topical formation at a concentration of about 1.0-10% (w/w). For example, the topical formulation may comprise about 1-1.5%, 1.5-2%, 2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, or 9.5-10% (w/w) of the viscosity increasing agent. Alternatively, the topical formulation may comprise about 1-5%, 2.5-7.5%, or 5-10% (w/w) of the viscosity increasing agent.

An "ointment base" can be any semisolid preparation or vehicle into which an active agent may be incorporated. Exemplary ointment bases include, but are not limited to, oleaginous ointment bases (e.g., white petrolatum or white ointment), absorption ointment bases (e.g., hydrophilic petrolatum, anhydrous lanolin, Aquabase™ Aquaphor®, and Polysorb®), water/oil emulsion ointment bases (e.g., cold cream, hydrous lanolin, rose water ointment, Hydrocream™, Eucerin®, and Nivea®), oil/water emulsion ointment bases (e.g., hydrophilic ointments, Dermabase™, Velvachol®, and Unibase®), and water-miscible ointment bases (e.g., polyethylene glycol (PEG) ointment and Polybase™). Ointment bases may be pharmacologically inert but can entrap water in order to provide an emollient protective film. In a specific embodiment, the ointment base may be any petrolatum compound (e.g., petrolatum, white petrolatum, white soft paraffin, liquid petrolatum, liquid paraffin). In a further specific embodiment, the ointment base is white petrolatum (CAS number 8009-03-8). The ointment base may be present in the topical formation at a concentration of about 5-30% (w/w), e.g., 10-30% (w/w). For example, the topical formulation may comprise about 5-25%, 5-20%, 5-15%, 5-15%, 10-15%, 15-20%, 20-25%, or 25-30% (w/w) of the ointment base. Specifically, the topical formulation may comprise about 5, 6, 7, 8, 9, 10, 11, 12, 13, 14, 15, 16, 17, 18, 19, 20, 21, 22, 23, 24, 25, 26, 27, 28, 29, or 30 percent (w/w) of the ointment base.

In some embodiments, the "ointment base" described herein contains less than 20% water and volatiles, and more than 50% hydrocarbons, waxes, or polyols as the vehicle.

In some embodiments, the "ointment base" described herein is a "cream base," which contains more than 20% water and volatiles and/or typically contain less than 50% hydrocarbons, waxes, or polyols as the vehicle for the drug substance. The cream base can be a multiphase preparation containing a lipophilic phase and an aqueous phase. In some instances, the cream base is a lipophilic cream base, which has a lipophilic phase as the continuous phase. Such a cream base usually contains water-in-oil emulsifying agents such as wool alcohols, sorbitan esters and monoglycerides. In other instances, the cream base is a hydrophilic cream base, which has an aqueous phase as the continuous phase. Such a cream base typically contains oil-in-water emulsifying agents such as sodium or trolamine soaps, sulfated fatty alcohols, polysorbates and polyoxyl fatty acid and fatty alcohol esters, which may be in combination with water-in-oil emulsifying agents, if needed.

An "antimicrobial preservative" can be any compound capable of destroying microbes, prevent the multiplication or growth of microbes, or prevent the pathogenic action of microbes. Exemplary antimicrobial preservatives include, but are not limited to, a paraben compound (an ester of para-hydroxybenzoic acid; e.g., paraben, methylparaben, ethylparaben, propylparaben, butylparaben, heptylparaben, benzylparaben, isobutylparaben, isopropylparaben, benzylparaben, or their sodium salts), benzalkonium chloride, benzethonium chloride, benzyl alcohol, boric acid, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. The antimicrobial preservative may be present in the topical formation at a concentration of about 0.005-0.2%, e.g., about 0.01-0.2% (w/w). For example, the topical formulation may comprise about 0.005-0.01%, 0.01-0.05%, 0.05-0.1%, 0.1-0.15%, or 0.15-0.2% (w/w) of the antimicrobial preservative. Specifically, the topical formulation may comprise about 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 percent (w/w) of the antimicrobial preservative.

An "emulsifying agent" is a compound or substance which acts as a stabilizer for a mixture of two or more liquids that are normally immiscible (unmixable or unblendable). Exemplary emulsifying agents may include, but are not limited to, natural emulsifying agents (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and Veegum [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, propylene glycol monostearate, and polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, and methylcellulose), sorbitan fatty acid esters (e.g., polyoxyethylene sorbitan monolaurate [Tween® 20], polyoxyethylene sorbitan [Tween® 60], polyoxyethylene sorbitan monooleate [Tween® 80], sorbitan monopalmitate [Span® 40], sorbitan monostearate [Span® 60], sorbitan tristearate [Span® 65], glyceryl monooleate, and sorbitan monooleate [Span® 80]), polyoxyethylene esters (e.g., polyoxyethylene monostearate [Myrj® 45], polyoxyethylene hydrogenated castor oil, polyethoxylated castor oil, polyoxymethylene stearate, and Solutol), sucrose fatty acid esters, polyethylene glycol fatty acid esters (e.g., Cremophor®), polyoxyethylene ethers (e.g., polyoxyethylene lauryl ether [Brij® 30]), and poly(vinylpyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, and docusate sodium, and/or combinations thereof. The emulsifying agent may be present in the topical formation at a concentration of about 0.5-10% (w/w), e.g., 0.5-6% (w/w). For example, the topical formulation may comprise about 0.5-1%, 1-1.5%, 1.5-2%, 2-2.5%, 2.5-3%, 3-3.5%, 3.5-4%, 4-4.5%, 4.5-5%, 5-5.5%, 5.5-6%, 5-10%, 6-10%, or 8-10% (w/w) of the emulsifying agent. Specifically, the topical formulation may comprise about 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 percent (w/w) of the emulsifying agent.

The topical formulation of the invention may further contain one or more solvents (e.g., non-water solvents or water). Exemplary non-water solvents may include, but are not limited to, any known solvent including propylene glycol, glycol, and mixtures thereof. The non-water solvent may be present in the topical formation at a concentration of about 2-65% (w/w). For example, the topical formulation may comprise about 2-15%, 15-30%, 30-45%, or 45-65% (w/w) of the solvent. In some embodiments, the topical formulation of the invention may also contain water.

In some embodiments, the topical formulation of the invention may further comprise one or more emollients, fragrances, or pigments. The topical formula may also be used in conjunction with a wound dressing (e.g., bandage with adhesive, plaster patch and the like). (e.g., cyclohexane, n-hexane, n-decane, i-octane, octane, butyl ether, carbon tetrachloride, triethyl amine, i-propyl ether, toluene, p-xylene, t-butyl methyl ether, benzene, benzyl ether, dichloromethane, methylene chloride, chloroform, dichloroethane, ethylene dichloride, 1-butanol, i-butyl alcohol, tetrahydrofuran, ethyl acetate, 1-propanol, 2-propanol, methyl acetate, cyclohexanone, methyl ethyl ketone (MEK), nitrobenzene, benzonitrile, 1,4-dioxane, or p-dioxane). In certain embodiments, the topical formulation includes a hydrogel.

The active ingredient may be, but is not limited to, human serum albumen, calcium, bovine thrombin, human Thrombin (hThrombin), rhThrombin, factor VIIa, factor XIII, recombinant Factor XIII (rFactor XIII), thromboxane A2, prostaglandin-2a, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor, keratinocyte growth factor, nerve growth factor, In certain embodiments, a topical formulation includes an antibiotic, including antimicrobial peptides (AMP). In general any antibiotic can be used with the disclosed composition or methods. Examples of antibiotics that can be used include but are not limited to aminoglycosides (such as amikacin, gentamicin, kanamycin, neomycin, netilmicin, streptomycin, tobramycin, and paromomycin); ansamycins (such as geldanamycin, and herbimycin); carbacephems (such as loracarbef, ertapenem, doripenem, imipenem/cilastatin, and meropenem); cephalosporins (such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and ceftobiprole); glycopeptides (such as teicoplanin and vancomycin); macrolides (such as azithromycin, clarithromycin, dirithromycin, erythromycin, roxithromycin, troleandomycin, telithromycin, and spectinomycin); monobactams (such as aztreonam); penicillins (such as amoxicillin, ampicillin, azlocillin, carbenicillin, cloxacillin, dicloxacillin, flucloxacillin, mezlocillin, meticillin, amoxycillin, clavamox, clavulanic acid, nafcillin, oxacillin, penicillin, piperacillin, and ticarcillin); peptides (such as bacitracin, colistin, and polymyxin b); quinolones (such as ciprofloxacin, enoxacin, gatifloxacin, levofloxacin, lomefloxacin, moxifloxacin, norfloxacin, ofloxacin, trovafloxacin, grepafloxacin, and sparfloxacin); sulfonamides (such as mafenide, prontosil (archaic), sulfacetamide, sulfamethizole, sulfanilimide (archaic), sulfasalazine, sulfisoxazole, trimethoprim, and trimethoprim-sulfamethoxazole); tetracyclines (such as demeclocycline, doxycycline, minocycline, oxytetracycline, and tetracycline); and others (such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin, thiamphenicol, and tinidazole) or combinations thereof.

Similar to the most therapeutic proteins, Serp-1 polypeptide may exhibit a short half-live and low stability. Thus in some embodiments, it may be desirable to control Serp-1 protein release in order to potentially extend the release time and increase stability for a long-term topical treatment, such as wound healing. To combat this potential problem, the inventors have formulated Serp-1 polypeptides with hydrogels to form slow release composition. Thus aspects of the disclosure are directed to hydrogels that include a Serp-1 polypeptide, or nucleic acid encoding a Serp-1 polypeptide, and optionally, other active ingredients as discussed above. In some examples the hydrogels are incorporated into a wound dressing for promoting wound healing. To this end, aspects of the disclosure are directed to wound dressings, and methods of using such wound dressings.

A hydrogel is a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as chitosan, alginate, polyphosphazenes, and polyacrylates such as hydroxyethyl methacrylate, which are crosslinked ionically, or block copolymers such as PLURONICS™ (BASF Corporation) or TETRONICS™ (BASF Corporation), polyethylene oxide-polypropylene glycol block copolymers which are cross-linked by temperature or pH, respectively. Other materials include proteins such as fibrin, polymers such as polyvinylpyrrolidone, hyaluronic acid and collagen.

The hydrogel may also include gelatin, cellulose, or collagen-based materials. In some examples, the gelatin-based substrate includes an absorbable sponge, powder or film of cross-linked gelatin, for example, GELFOAM® (Upjohn, Inc., Kalamazoo, Mich.) which is formed from denatured collagen. A cellulose-based substrate includes an appropriate absorbable cellulose such as regenerated oxidized cellulose sheet material, for example, SURGICEL® (Johnson & Johnson, New Brunswick, N.J.) or Oxycel® (Becton Dickinson, Franklin Lakes, N.J.). Collagen materials can include an appropriate resorbable collagen, such as purified bovine corium collagen, for example, AVITENE® (MedChem, Woburn, Mass.), HELISTAT® (Marion Merrell Dow, Kansas City, Mo.), HEMOTENE® (Astra, Westborough, Mass.), or SURGIFOAM® (Johnson & Johnson, New Brunswick, N.J.). There have been prior success with the application of a chitosan bandage (see for example, HemCon®, Tricol Biomedical Inc.) for wound healing. Chitosan-based hydrogels, such as chitosan-collagen hydrogel, have also been tested for wound treatment for delivery of antimicrobials, peptides, and growth factors showing significant promotion on wound healing (Liu et al., RSC Adv. (2018). doi:10.1039/c7ra13510f, Elviri et al., Expert Opin. Drug Deliv. (2017). doi:10.1080/17425247.2017.1247803, Hamedi et al., Carbohydr. Polym. (2018). doi:10.1016/j.carbpol.2018.06.114, Riva et al., Adv. Polym. Sci. (2011). doi:10.1007/12_2011_137, Liu et al., Adv. Polym. Sci. (2011). doi:10.1007/12_2011_118). Considering the biocompatible, antimicrobial, biologically adhesive, hemostatic effect and applications for drug delivery, a chitosan-based hydrogel as a drug delivery system for the treatment of wound healing with Serp-1 is disclosed herein. In addition to the discovery of function of Serp-1 in promoting accelerated wound healing as reported herein, a chitosan-collagen hydrogel carrier can efficiently deliver Serp-1 locally to a wound site and promote healing. Thus, in some embodiments, the a Serp-1 polypeptide, or nucleic acid encoding a Serp-1 polypeptide (and other active ingredients as discussed above) are incorporated into a chitosan-collagen hydrogel carrier.

Figure 8:
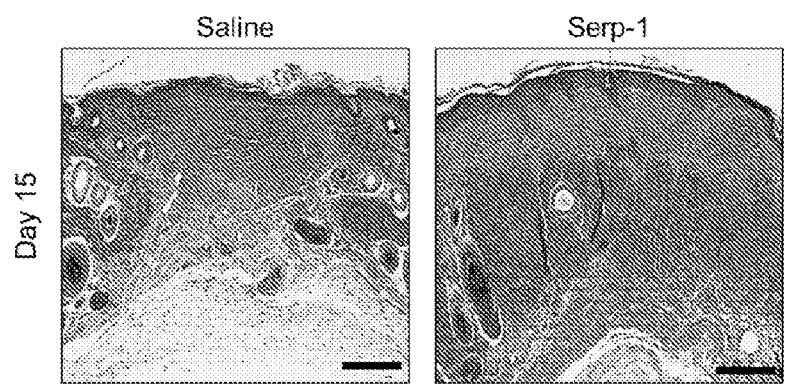
FIG. 8 is a set of digital images showing Serp-1 treatment promotes the collagen maturation in wounds. Representative images of Herovici's stained wound tissue at day 15. Blue stain indicates younger collagen (Type 3); Red/pink stain indicates mature collagen (Type 1).

During wound healing, collagen accumulation and organization are correlated with scar formation. Collagens play a crucial role in angiogenesis during tissue regeneration. It is well known that collagen I a central factor allowing for endothelial cells to initiate precapillary cord formation. In contrast increased deposition of collagen III reduces the density of blood vessels at sites of wound healing (Davis and Senger et al., Circ. Res. (2005). doi:10.1161/01.RES.0000191547.64391.e3, O'Rourke et al., Adv. Wound Care. (2018). doi:10.1089/wound.2018.0827). By differentially staining different types of collagens using Herovici's stain, it was found that Serp-1 treatment affected collagen organization and maturation within the healing tissue by increasing the ratio of collagen III to collagen I in treated wound (FIG. 8).

In certain embodiments, the wound dressing that includes a Serp-1 polypeptide or nucleic acid encoding a Serp-1 polypeptide is formed of a biomaterial, such as poly [β-(1-4)-2-amino-2-deoxy-D-glucopyranose], more commonly referred to as chitosan optionally in combination with collagen, e.g. collagen-chitosan hydrogels. The wound dressing can be formed into a sponge-like or woven configuration via the use of an intermediate structure or form producing steps. The biomaterial comprises an interconnected open porous structure, and/or an oriented open lamella structure, and/or an open tubular structure, and/or an open honeycomb structure, and/or a filamentous structure.

Methods for Promoting Wound Healing

Any of the topical formulations described herein can be used for promoting wound healing in a subject in need of the treatment. The topical formulation may be applied to a wound site following a suitable dosage and treatment regimen. The dosage and administration regimen for the described method will depend on the nature and condition of the wound being treated, the age and condition of the patient, and any prior or concurrent therapy. In some instances, the topical formulation can be applied once every week, once every other day, once daily, twice daily, three times daily, or four time daily for a suitable period of time. The treatment may be terminated when the wound is recovered. When necessary, the treatment may resume, for example, if a wound recurs.

The term "wound" refers to an injury to living tissue caused by a cut, blow, or other impact (e.g., caused by a medical condition such as a skin disorder), typically one in which the skin is cut or broken. Wound may be associated with a medical condition, for example, a skin disorder. The term "wound healing" denotes the dynamic and complex process of replacing devitalized or missing cellular structures and/or tissue layers. The term "promotion of wound healing" or "promoting wound healing" denotes the inducement of an increased level or rate of replacement for devitalized or missing cellular structures and/or tissue layers. As an example, promotion of wound healing may be indicated by partial or complete ulcer closure or an increase in the healing rate of an ulcer (including but not limited to more rapid changes in ulcer size, area, or severity, a more rapid closure of the ulcer, and/or an increase in the percentage change from baseline in ulcer size, area, or severity when compared to a control ulcer treated with a placebo).

The subject to be treated by the topical formulation can be a human or a non-human mammal. In some embodiments, the subject is a human patient having an open wound, which refers to an injury or damage to living tissues (e.g., skin) that cause a disruption in the normal continuity of biological structures. An open wound may include, but is not limited to, an abrasion, incision, laceration, puncture, avulsion, cut, or other similar injuries.

In other embodiments, the subject is a human patient having a chronic wound, which can be injuries or damage to living tissues (e.g., skin) that cause a disruption in the normal continuity of biological structures and do not heal in an orderly set of stages and/or in a predictable amount of time. A chronic wound may include, but is not limited to: a surgical wound, a traumatic wound, a pressure ulcer, a venous ulcer, or a diabetic ulcer. In other examples, a chronic wound may be associated with a disease or disorder, for example, a carcinoma, burn, bedsore, a skin disorder such as atopic dermatitis.

In one example, the subject is a human patient having foot ulcer associated with diabetes (e.g., type I or type II). Diabetes mellitus (also known as diabetes) is a group of metabolic diseases which result in high blood sugar levels over a prolonged period. Diabetes may result from the pancreas not producing enough insulin or the cells of the body not responding properly to the insulin produced. The three main types of diabetes mellitus are Type I (also known as "insulin-dependent diabetes mellitus" (IDDM) or "juvenile diabetes"; results from the failure of the pancreas to produce enough insulin), Type 2 (also known as "non-insulin-dependent diabetes mellitus" (NIDDM) or "adult-onset diabetes"; results from the failure of cells to respond to insulin properly), and gestational diabetes (seen during pregnancy when high blood sugar levels are observed in the absence of a previous history of diabetes). Many serious complications are observed in diabetic patients including, but not limited to, chronic wounds such as diabetic foot ulcers (also known as diabetic ulcers).

In some embodiments, the subject to be treated by the methods described herein suffers from a severe wound, for example, having an ulcer with an area greater than 2 $cm^2$ (e.g., 3 $cm^2$, 4 $cm^2$ or 5 $cm^2$). In some examples, the subject suffers from one or more plantar ulcers.

Kits for Use in Promoting Wound Healing

The present disclosure also provides kits for use in promoting wound healing. Such kits may include one or more containers comprising a topical formulation as described herein, which comprises a disclosed Serp-1 polypeptide and/or a nucleic acid molecule encoding a disclosed Serp-1 polypeptide.

In some embodiments, the kit may comprise instructions for use in accordance with any of the methods described herein. The included instructions may comprise a description of administration of the topical formulation to promote wound healing according to any of the methods described herein. The kit may further comprise a description of selecting an individual suitable for treatment based on identifying whether that individual has wounds in need of treatment.

The instructions relating to the use of a topical formulation generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for promoting wound healing. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. At least one active agent in the composition is an active agent selected from the group consisting of a Serp-1 polypeptide and/or a nucleic acid molecule encoding a disclosed Serp-1 polypeptide.

Kits may optionally provide additional components such as interpretive information. Normally, the kit comprises a container and a label or package insert(s) on or associated with the container. In some embodiments, the invention provides articles of manufacture comprising contents of the kits described above.

EXAMPLE

Materials and Methods

Proteins and Chemicals

Figure 1B:
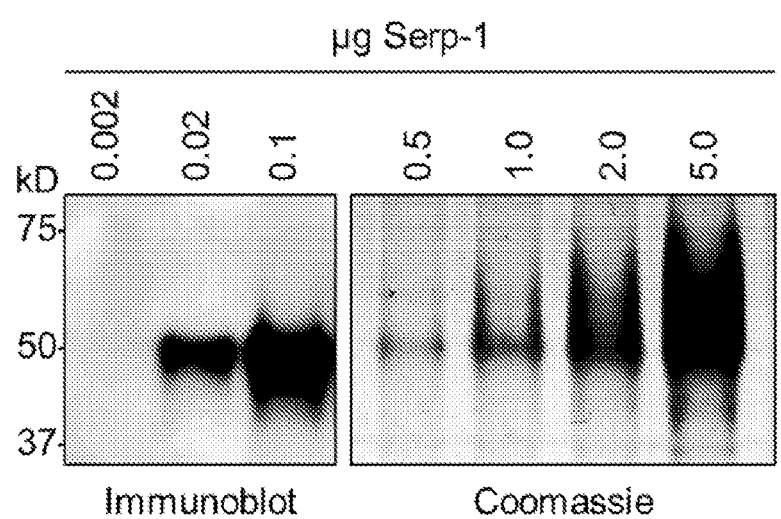
FIG. 1B shows digital image of an immunoblot (left) and Coomassie (right) validation of recombinant cGMP Serp-1 using an anti-Serp-1 mouse monoclonal antibody.

Recombinant Serp-1 (m008.1L; NCBI Gene ID #932146) was expressed and secreted by a Chinese hamster ovary (CHO) cell line (Viron Terapeutics Inc., London, ON). GMP-compliant purification was performed by sequential column chromatographic separation with greater than 95% purity as determined by Coomassie-stained SDS-PAGE and reverse-phase HPLC (FIG. 1B). Serp-1 was endotoxin-free by LAL assay. Anti-Serp-1 mouse monoclonal antibody was produced and provided by Viron Therapeutics.

Type I collagen solution (C3867-1VL) and low molecular weight chitosan (4488691; 75-85% deacetylated) were obtained from Sigma-Aldrich (St. Louis, MO).

All chemicals for Trichrome staining, including phosphomolybdic/phosphotungstic acid solution, Biebrich scarlet solution 1%, aniline blue solution, Bouin's fixative, acetic acid 1% aqueous, Weigerts iron hematoxylin A and B were from EMS (Electron Microscopy Sciences, Hatfield, PA). Heerovici's collagen stain kit was from American Master-Tech (Lodi, CA). Hematoxylin and eosin for H&E stain were from Sigma-Aldrich.

Information about each antibody used in this study is provided below when first mentioned.

Animals

Male and female wildtype C57BL6/J mice aged 8-12 weeks were used in this study. Mice were kept on a standard 12/12 light-dark cycle in specific pathogen-free housing conditions and given food and water ad libitum. Mice were single-housed after the wounding procedure to prevent interference with wound healing. Information about all mouse groups in this study are detailed in Table 1.

TABLE 1

Numbers of C57BL6/J mice used in this study

| Treatment | Days follow-up | Number of mice |
| --- | --- | --- |
| Saline | 1 | 2 |
| Saline | 4 | 2 |
| Saline | 7 | 2 |
| Saline | 15 | 13 |
| Serp-1 - 2 µg | 15 | 6 |
| Serp-1 - 1 µg | 15 | 7 |
| Serp-1 - 1 µg + 1 µg | 1 | 2 |
| Serp-1 - 1 µg + 1 µg | 4 | 2 |
| Serp-1 - 1 µg + 1 µg | 7 | 2 |
| Serp-1 - 1 µg + 1 µg | 15 | 5 |
| Hydrogel$^a$ w/Saline | 15 | 4 |
| Hydrogel$^a$ w/Serp-1 | 15 | 4 |

$^a$Chitosan-collagen hydrogel

Wounding Surgery and Measurement

The mouse dermal wound healing splinted model was used for these studies where the contraction is held by a donut-shaped splint remains the most widely accepted and extensively used model to study skin wound healing in mice (Galiano et al., Wound Repair Regen. 12 (2004) 485-492. doi:10.1111/j.1067-1927.2004.12404.x, Wang et al., Nat. Protoc. 8 (2013) 302-309. doi:10.1038/nprot.2013.002, Dunn et al., J. Vis. Exp. (2013) 1-6. doi:10.3791/50265).

Mice (N=29 mice) were anesthetized by intraperitoneal injection of a cocktail of 120 mg/kg ketamine and 6 mg/kg xylazine, 0.1 ml/25 g bodyweight and prepped by shaving an area of approximately 1×1 inch spanning from between the ears to the peak of the spine, centered between each shoulder. The shaved area was sterilized by two washes with 2% chlorhexidine gluconate solution (Dyna-Hex 2®, Xttrium Laboratories) and 70% ethanol using cotton swabs.

A 3.5 mm punch biopsy was performed centered in the shaved area to create the full-thickness wound excision. Treatment or control as saline solution or chitosan-collagen hydrogel preparation were applied to the wound using a hand-held micropipette. In brief, 13 mice were given saline inoculation at the time of injury, 6 mice were given Serp-1 at the time of injury at doses or 1 or 2 µg. Six mice were given 1 μg of Serp-1 and followed by second bolus at 3 days post wounding. A second group of 6 mice were given Serp-1/chitosan treatment applied at the time of injury and 6 mice were given chitosan gel alone.

A donut-shaped silicon splint (O.D. 15 mm; I.D. 5.0 mm; Culture-Well™ Grace Biolabs) with Tegaderm™ (3M Company) affixed to one side was coated with cyanoacrylate glue (Krazy Glue®) on the opposite side and carefully placed on the back of the mouse with the biopsy site centered within the inner hole. Six interrupted sutures (4-0 black Ethilon monofilament with a FS-2 reverse cutting needle; Ethicon, Inc.) were placed around the outer edge of the splint to complete the procedure. Mice were allowed to recover and returned to single-housed cages for the remainder of the trial.

On the day of the procedure (Day 0) and on every subsequent day of follow-up, for a total of 15 days, mice were collected and wounds assessed while awake. Digital images were collected using a Google Pixel model 1 or 3XL smartphone camera. Planimetric measurements of wound healing progress was performed in Image)/FIJI and calibrated to known pixel-to-size measurements (Schindelin et al., Nat. Methods. 9 (2012) 676-682. doi:10.1038/nmeth.2019).

Preparation of Chitosan-Collagen Hydrogels with/without Serp-1

The procedure of prepare chitosan-collagen hydrogel was modified from the method of Rao (Rao et al., Proc. Natl. Acad. Sci. (2018). doi:10.1073/pnas.1804735115). Low molecular weight chitosan was swollen by adding 10 mg chitosan to 10 mL of deionized water and rotating overnight at 4° C. The excess water was removed from the mixture after spin down at 1,000 g for 15 min and the swollen chitosan product was frozen at −20° C. for 8 hours followed by incubation overnight at 4° C. Serp-1 (30 μg) was added and the mixture was rotated at 4° C. for 8 hours and then lyophilized overnight. Right before treatment or in vitro assays, the lyophilized product was added to Type I collagen solution (Sigma Life Science, C3867-1VL) to a total volume of 300 μA to form a chitosan-collagen/Serp-1 gel at a concentration of 1.0 μg Serp-1 per 10 μL gel.

Scanning Electron Microscopy (SEM) Imaging

Collagen-chitosan hydrogels were fixed in 2% glutaraldehyde at room temperature for 15 minutes. Fixed hydrogels were washed 3× in deionized water for 10 minutes each. Washed hydrogels were dehydrated in a graded ethanol series (30%, 50%, 75%, 95% and 3×100% anhydrous) at room temperature for 10 minutes each. Dehydrated hydrogels were then critical-point dried using liquid $CO_2$ as the transition fluid in a Balzers CPD-020 drying apparatus. Samples were then mounted on Al stubs and sputter-coated with gold for 5 minutes at 8 mA current in a Technics Hummer-II sputter coater, resulting in a coating of approximately 10 nm thickness. Samples were then imaged in a JEOL 6300 SEM operated at 15 kV with images acquired with an IXRF Systems Model 500 digital processor.

In Vitro Protein Release Assay

Three kind of hydrogels containing 0, 1.0 μg and 3.0 μg Serp-1 per 10 μL gel, respectively, were prepared as mentioned above. Thirty μL of gel aliquot per well was loaded into a 96-well plate, 4 wells for each gel. Two hundred μL, of saline containing 0.01% (w/v) sodium azide was added to each well and incubated at 37° C. At each designated time point, 20 μL of the incubating solution was collected from each well followed by adding 20 μL of fresh saline back into the same well. At day 4, gels were boiled with 200 μL of 1×SDS-loading dye after completely removing liquid from wells. Serp-1 released from gel or remained in gel were analyzed by western blotting.

H&E and Immunohistochemistry

Skin tissues were collected at day 1, 4, 7 and 15 and fixed in 10% neutral-buffered formalin for at least two days before tissue processing with a Leica TP1050 and embedded in paraffin with a Leica EG1160 embedding station. Blocks were serially sectioned using a Leica RM2165 microtome (4 μm sections) and stained with hematoxylin and eosin (H&E) by standard procedure. Sections were additionally stained by immunohistochemistry (IHC) for CD31 (Abcam, #ab28364, 1:100), Ly6G (Invitrogen, #14-5931-82, 1:100), and arginase-1 (Cell Signaling, #93668, 1:200), and with Masson's trichrome (Masson, J Tech Methods. 12 (1929) 75-90) and Herovici's polychrome (Herovici, Stain Technol. 38 (1963) 204-6, Levame and Meyer, Pathol. Biol. (Paris). 35 (1987) 1183-8) as special stains for collagen.

Imaging and Analysis

Slides were imaged on an Olympus BX51 upright microscope equipped with an Olympus DP74 high-resolution camera operated by cellSens Dimensions v1.16. Images were collected as objective-calibrated TIFFs and subsequently analyzed and processed in Image)/FIJI (Schindelin et al., Nat. Methods. 9 (2012) 676-682. doi:10.1038/nmeth.2019). Positively stained cells were counted per high power field for each treatment group.

Quantitative collagen texture analysis was performed in Image)/FIJI (Schindelin, Nat. Methods. 9 (2012) 676-682. doi:10.1038/nmeth.2019). Briefly, images were deconvoluted with the plugin "Colour Deconvolution 1.7" using the methods described by Ruifrok and Johnston (Ruifrok, Anal. Quant. Cytol. Histol. 23 (2001) 291-9). Local thickness of collagen bundles was determined with the plugin "LocalThickness 4.0.2" using the methods described by Saito and Toriwaki (Saito, Pattern Recognit. 27 (1994) 1551-1565. doi:10.1016/0031-3203(94)90133-3), and by Hildebrand and Rüegsegger (Hildebrand, J. Microsc. 185 (1997) 67-75. doi:10.1046/j.1365-2818.1997.1340694.x.). Regularity of collagen bundles was determined with the plugin "Directionality" as previously reported (Sensini, Biofabrication. 9 (2017) 015025. doi:10.1088/1758-5090/aa6204).

Western Blot

Samples boiled in Laemmli buffer were resolved on a 10% SDS-PAGE gel and transferred to a 0.2 μm pore Immun-Blot® PVDF membrane (Bio-Rad) using a Trans-Blot® SD apparatus (Bio-Rad). The membrane was briefly washed in PBS before blocking in 5% non-fat dry milk in 0.1% TBST (blocking buffer) for 1 hour at room temperature. Primary antibody against Serp-1 (1:2000) was incubated with the membrane overnight at 4° C. in blocking buffer. After washing, HRP-conjugated secondary antibody (1:2000) was incubated with the membrane in blocking buffer for 1 hour at room temperature. Membranes were developed with either ECL Start or Prime (Amersham) and imaged on an ImageQuant LAS4000 (GE Healthcare) on the increment/high resolution setting. Images were analyzed and processed with Image)/FIJI (Schindelin et al., Nat. Methods. 9 (2012) 676-682. doi:10.1038/nmeth.2019).

Statistics

Statistical significance analysis was performed by T-test with GraphPad Prism v8. P-values<0.05 was considered significant.

Results

Serp-1 Promotes Accelerated Wound Healing in Mouse Skin Wound Models.

Figure 2A:
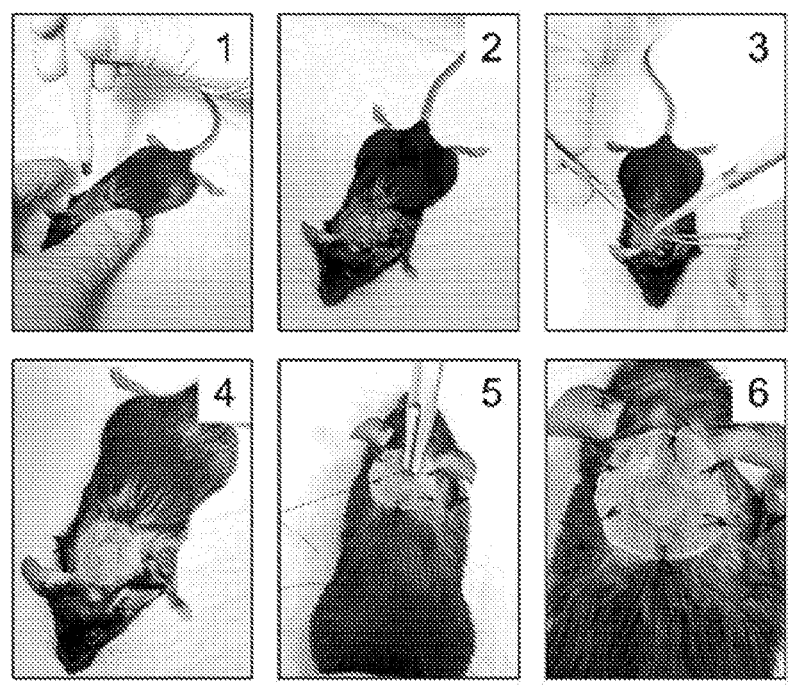

Serp-1 has proven to be an effective modulator of coagulation pathways and immune responses in numerous animal models of vascular injury and transplant. Serp-1 also proved safe in a Phase 2A clinical trial given by intravenous bolus injections after coronary stent implants in patients with unstable angina (Tardif et al., Circ. Cardiovasc. Interv. 3 (2010) 543-8. doi:10.1161/CIRCINTERVEN-TIONS.110.953885). In this study, the efficacy of topical Serp-1 application was tested in a full-thickness excisional model of wound healing (FIG. 2A). A 3.5 mm biopsy punch was used to create a full thickness dorsal skin wound in C57BL6/J wildtype mice. Wounds were produced through the entirety of the dermis without puncturing the panniculus carnosus. In an initial analysis, Serp-1 was applied in saline solution and compared to control saline solution alone, given directly to the wound bed. A silicone splint with a gas-permeable Tegaderm layer was sutured over the bed. The silicone splint prevented wound contraction, allowing direct visualization and photography of wound re-epithelialization during the course of a 15-day healing period (FIG. 2B).

Figure 2C:
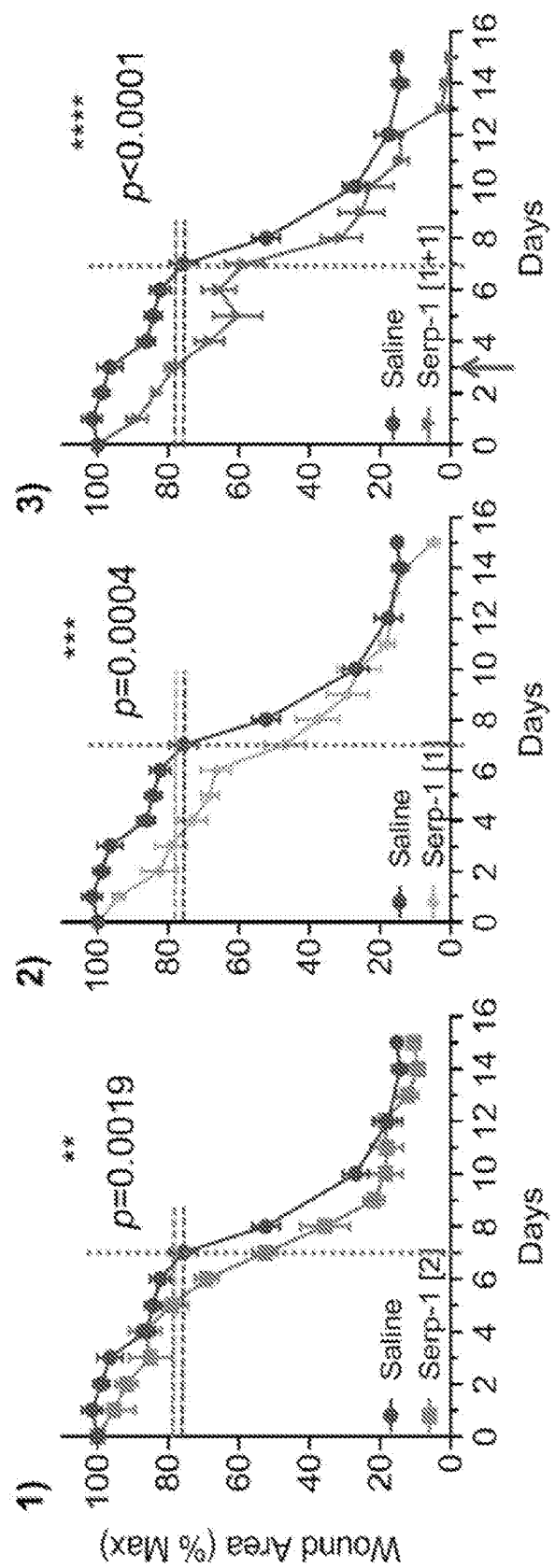
FIG. 2C is a series of graphs that show the full course of wound healing for mice with full-thickness wounds treated with saline alone or Serp-1 at a dose of (C-1) 2 µg/mouse (Serp-1 [2]), (C-2) 1 µg/mouse (Serp-1 [1]) or (C-3) 1 µg/mouse on Days 0 and 3 (Serp-1 [1+1]). Dotted horizontal cross lines indicate equivalent healing of Serp-1 [1+1] mice on Day 3 as is achieved by saline alone on Day 7.

The initial dose of Serp-1 applied to the wounds was 2 μg/mouse. This concentration was chosen due to the previously utilized 100 μg/kg/bodyweight (bw) concentration used in intraperitoneal applications of Serp-1 for prior mouse models, equating to 2 μg for a 20 g mouse (Chen, Antimicrob. Agents Chemother. 57 (2013) 4114-4127. doi: 10.1128/AAC.02594-12). We found that Serp-1 at a dose of 2 μg/mouse dose accelerated wound healing by approximately 3 days (FIG. 2C-1; p<0.0001).

Modifying of Serp-1 Dose and Application Timing of Application Further Improves Wound Healing Serp-1 is a purified recombinant protein with a short half-life and, like other serpins, is expected to have sensitive structural metastability (Huntington, J. Thromb. Haemost. 9 (2011) 26-34. doi:10.1111/j.1538-7836.2011.04360.x). Therefore, we examined the effect of repeated dosing and application times for Serp-1 treatments on the promotion of wound healing. We tested Serp-1 treatment at two doses, 1.0 μg or 2.0 μg/20 μL saline/10 mm² wound/mouse. We also tested repeat application of Serp-1 given as a 1.0 μg/20 μL saline/10 mm² wound/mouse at day 0 and day 3, respectively. From data shown in FIG. 2C, Serp-1 significantly promotes wound closure. The group treated with 2.0 μg of Serp-1 had greater than 20% closure at day 5, while the control group (saline only) needed 7 days to achieve similar healing closure where the treated group had achieved 47% closure (FIG. 2C-1). Interestingly, when the Serp-1 dose was reduced to 1.0 μg/wound/mouse, faster closure was observed for the treated group where mice needed a mean of 3 days less to achieve the same degree of closure as control group at day 7 or for the higher dose Serp-1 (2.0 μg) at day 5, respectively (FIGS. 2C-1 and C-2). Comparing to the saline group, treatment with 1.0 μg Serp-1 treatment led to wound closure four days earlier in the first week. When we gave mice a second application after 3 days treatment with 1.0 μg/wound dosage, wound healing was further enhanced with 40% wound closure at day 5. In contrast there was only 20% wound closure in saline treated controls and 30% in single dose treatment groups (FIG. 2B, C). During the 15 days of observation, the repeated treatment group also had more completely closure than other groups. Thus, the data demonstrates that the dose and timing of treatment for Serp-1 can affect the efficacy of this protein to promote wound healing on the mouse model.

Serp-1 can be Efficiently Released from Chitosan-Collagen Hydrogel In Vitro.

Figure 3C:
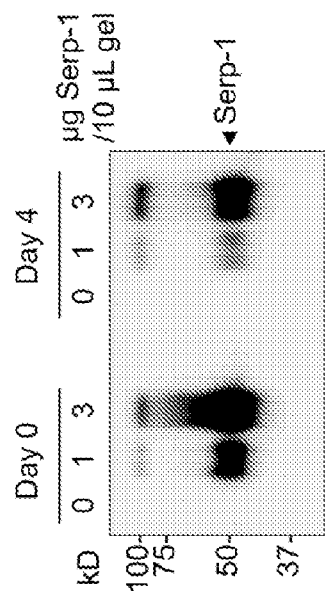
FIGS. 3A-3C show the development and characterization of chitosan-collagen hydrogel carrying Serp-1.
Figure 3B:
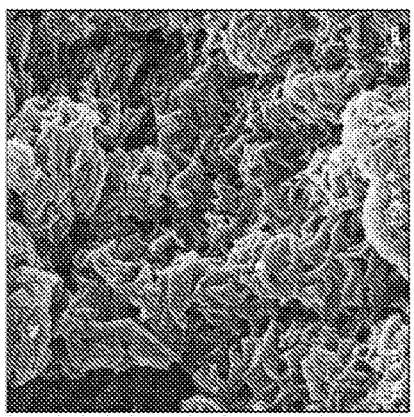
Figure 3A:
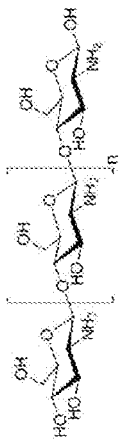

Protein factors and cytokines, including vascular endothelial growth factor (VEGF) and recombinant human epidermal growth factor (rhEGF) are now considered attractive as biologic therapeutics, but these same protein reagents also suffer from poor stability, due to proteolytic and chemical degradation as well as physical unfolding and aggregation. This limit becomes more obvious when proteins are applied over a longer term to promote wound healing. Hydrogels have been developed to enhance the stability and sustained delivery of therapeutic proteins at wound sites (Vermonden, Chem. Rev. (2012). doi:10.1021/cr200157d, Pachuau, Expert Opin. Drug Deliv. 12 (2015) 1895-1909. doi: 10.1517/17425247.2015.1070143). Serp-1 is a member of the serpin superfamily of proteins, which is characterized by a highly sensitive metastability, a key characteristic of serpin function (Mahon, Biochemistry. 57 (2018) 1096-1107. doi: 10.1021/acs.biochem.7b01171, Huntington, J. Thromb. Haemost. 9 (2011) 26-34. doi:10.1111/j.1538-7836.2011.04360.x, Huntington, J. Mol. Biol. 293 (1999) 449-455. doi:10.1006/jmbi.1999.3184). This metastability may also result in potential polymerization under certain stresses, including chemical modification (Huntington, Methods Enzymol. (2011). doi:10.1016/B978-0-12-385950-1.00017-1). Thus, we developed a non-covalently cross-linked composition of chitosan and collagen as a carrier for maintaining stability and sustained delivery of Serp-1. When prepared, the homogenously mixed type I collagen solution and Serp-1-bound chitosan form a translucent, spreadable gel (FIG. 3A). Ultrastructural analysis by scanning electron microscopy revealed a highly complex appearance, with many regularly dispersed folds, demonstrating that the hydrogel had a high capacity surface area for potential protein binding (FIG. 3B). We verified the dose-dependent, sustained release of Serp-1 from the chitosan-collagen hydrogel into aqueous solution in vitro with minimal dimerization (FIG. 3C).

Delivery of Serp-1 Through Chitosan-Collagen Hydrogel Significantly Promotes Wound Healing on Mouse Model.

After demonstrating that delivery of stable Serp-1 protein was sustained by the chitosan-collagen hydrogel release in vitro, the therapeutic efficacy was subsequently tested in the mouse dorsal wound model by topical application of 30 μl of gel containing 3.0 μg Serp-1 onto the wound at day 0 (FIG. 4A). The gel was directly loaded onto the wound surface by sterile pipette tip and covered by silicon splint and Tegaderm (see Materials and Methods). Compared to wounds treated with saline or chitosan only, wounds treated with Serp-1 gel had similar closure rates as for wounds treated with 1.0 μg of Serp-1 followed by a bolus at day 3 (FIG. 4B). When the chitosan-collagen carrier remaining on the granulation tissue after 4 days application was collected and performed Western blot assay to assess for residual Serp-1, 20% Serp-1 remained on the surface indicating 80% Serp-1 was released from gel during wound healing (FIG. 4C). This data indicates that sustained release of Serp-1 by chitosan-collagen hydrogel after a one-time application was capable of significantly promoting wound healing.

Serp-1 Promotes Vascularization During Wound Healing.

New blood vessel formation, i.e. vascularization, is a critical component of wound healing. Thus numerous strategies have been developed to promote increased vascularization at sites of skin wounds (Tonnesen et al., J. Investig. Dermatology Symp. Proc. (2000). doi:10.1046/j.1087-0024.2000.00014.x, Veith et al., Adv. Drug Deliv. Rev. (2018). doi:10.1016/j.addr.2018.09.010). Serp-1 as a serpin has been demonstrated to bind and inhibit uPA, uPAR complexes. The fibrinolytic proteases can release connective tissue stores of growth factors as well as inhibition matrix degrading enzymes (matrix metalloproteinases or MMPS) which can alter both inflammation as well as revascularization.

Figures 5A, 5B:
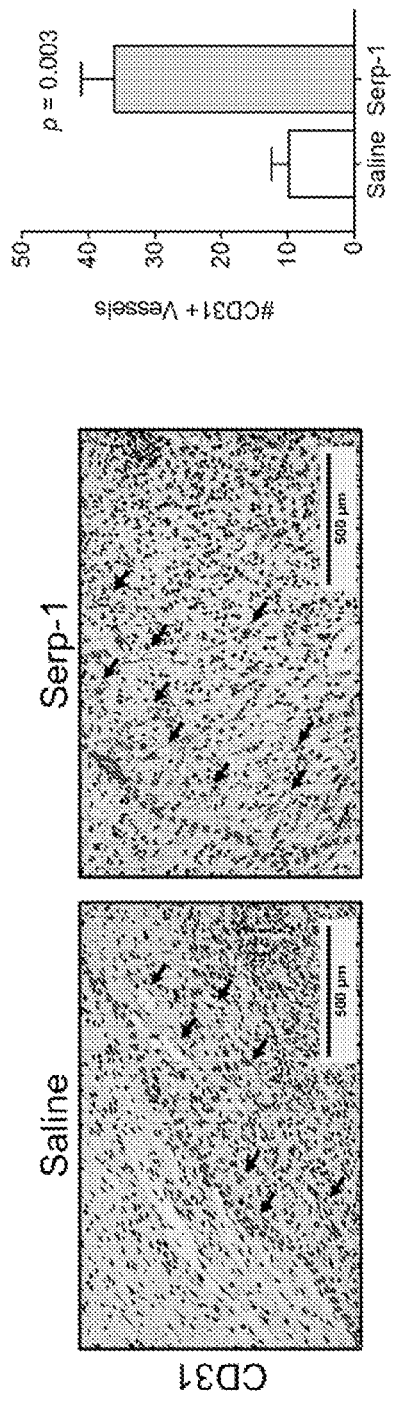
FIGS. 5A-5B show that Serp-1 enhances peri-wound vascularization.

New vessel growth was examined for vascularization at 7 days after wounding, an intermediate time at which the wounds were observed to begin healing at a high rate (FIG. 1C). The blood vessels were analyzed by immunohistochemistry with antibodies against the endothelial marker CD31 (also called PECAM-1), a marker for endothelial cells commonly used to indicate wound bed blood vessels (Vanchinathan et al., Am. J. Clin. Pathol. (2015). doi: 10.1309/AJCPRHM8CZH5EMFD). The number of positive staining vessels in different optical fields was quantified from four pairs of saline- and Serp-1-treated wounds. It was first noted that Serp-1-treated mice had appreciably more "mature" CD31-positive vessels, with increased length and thickness versus mice treated with saline alone (FIG. 5A). Quantitatively, vessel density was significantly increased in the pen-wound area of mice treated with Serp-1 (FIG. 5B). The number of vessels each image is 36.3±4.9 in Serp-1 treated mice versus 10.0±2.5 in the saline control mice.

Serp-1 Treatment Promotes Neutrophil Infiltration and M2 Macrophage Differentiation During Wound Healing.

Neutrophils are one of the most abundant cells of the immune system and these cells are recruited to wound sites very early after damage and remain active in early phases of wound healing (Wilgus et al., Adv. Wound Care. (2013). doi:10.1089/wound.2012.0383, Landén et al., Cell. Mol. Life Sci. (2016). doi:10.1007/s00018-016-2268-0, Wang, Cell Tissue Res. (2018). doi:10.1007/s00441-017-2785-7). In addition to cleaning the wound sit and removing damaged tissues, neutrophils have an important role in promoting skin wound healing through fibroblast repopulation, new vessel formation, keratinocyte migration and proliferation, but they need to be under dedicated control.

Therefor neutrophil infiltration was analyzed at sites of wound healing with and without treatment with Serp-1 at day 4 by immunohistochemistry with antibodies against Ly6G (FIG. 6A). There is non significant trend toward an increase of Ly6G positive cells in the healing tissues treated with Serp-1 (p=0.110) (FIG. 6B).

Additionally the differentiation of M2 macrophages was =analyzed (FIG. 6C), during wound-healing (Kotwal and Chien, Macrophage differentiation in normal and accelerated wound healing, in: Results Probl. Cell Differ., 2017. doi:10.1007/978-3-319-54090-0_14), by IHC with antibodies against Arginase-1 (EC3.5.3.1). Arginase is considered a prototypic M2 marker in mouse (Roszer, Understanding the mysterious M2 macrophage through activation markers and effector mechanisms, Mediators Inflamm. (2015). doi: 10.1155/2015/816460). Arg-1 positive macrophages in Serp-1 treated wounds at day 4 had significantly increased density when compared to control wounds. Even at day 7 when M2 macrophages in untreated wounds reached peak levels, the density in Serp-1 treated wound still had significant higher (FIG. 6D).

Serp-1 Treatment Reduces Scarring.

During wound healing, collagen accumulation and organization are correlated with scar formation. Masson's trichrome staining (FIG. 7A) and Herovici's staining (FIG. 8) was performed to study the dermal collagen fibers after 15 days wound healing. Local scar thickness (FIG. 7C) and directionality (FIG. 7D) of collagen in scars were analyzed using ImageJ after Masson's trichrome staining under microscopic examination (20× magnification). With Serp-1 treatment, collagen fibers demonstrated increased bundle thickness as well as more organized directionality, with close similarity to the same features found in the collagen network of normal skin. Conversely, skin of mice treated with saline alone demonstrated limited maturation as indicated by small bundle thickness, as well as reduced directionality, indicative of poorly organized collagen deposition and characteristic of scar architecture (Zhang, Burn. Trauma. 3 (2015) 1-8. doi:10.1186/s41038-015-0013-9, Osman, BMC Bioinformatics. 14 (2013) 1. doi:10.1186/1471-2105-14-260).

Collagens play a crucial role in angiogenesis during tissue regeneration. It is well known that collagen I a central factor allowing for endothelial cells to initiate precapillary cord formation. In contrast increased deposition of collagen III reduces the density of blood vessels at sites of wound healing (Davis, Circ. Res. (2005). doi:10.1161/01.RES.0000191547.64391.e3, O'Rourke, Adv. Wound Care. (2018). doi:10.1089/wound.2018.0827). We sought to further investigate the quality of the collagen in the healed wounds by Herovici's staining, a specialized method to differentiate between young (Type 3, more blue) and mature (Type 1, more red/pink) collagen bundles (Herovici, Stain Technol. 38 (1963) 204-6, Levame, Pathol. Biol. (Paris). 35 (1987) 1183-8). Whereas saline-treated wounds displayed primarily a blueish hue in the connective tissue by Herovici's stain, Serp-1-treated wounds were substantially more reddish hued, indicating a greater degree of maturation in the collagen bundles of Serp-1-treated mice (FIG. 8). Taken together, these data demonstrate that in addition to more rapid wound healing, the quality of the healed wound site is improved versus saline treatment and more similar to that of normal, unwounded skin.

CONCLUSION

A chitosan-based hydrogel was developed for the local delivery of a viral immunomodulatory protein, Serp-1, to promote accelerated wound healing. Our findings demonstrate that Serp-1 can significantly promote wound healing in a mouse model with a 40% faster closure rate as well as a reduction in scarring. Similar to other proteins used for therapeutics, the dose and application method modulated the efficacy of Serp-1 in this model. Multiple applications with lower dose of Serp-1 (1.0 µg/wound) had improved efficacy versus a single application with higher dose (2.0 µg/wound) (FIG. 2). Using a chitosan-collagen spreadable hydrogel as the carrier to topically deliver Serp-1, a single application achieved the similar result as that of multiple applications, but avoided the need to disturb the wound bed, which may be considered a possible source of secondary injury during wound management. This study not only established the advantage of using a unique viral immunomodulator, Serp-1, to promote accelerated wound healing with reduced scar formation, but also demonstrated the possibility of using a chitosan-collagen spreadable hydrogel to efficiently deliver therapeutic protein factors with minimal application and secondary wound perturbation.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

We claim:

1. A topical formulation, comprising:

an effective amount of a Serine Protease Inhibitor-1 (Serp-1) polypeptide, wherein the Serp-1 polypeptide comprises a reactive center loop comprising an amino acid sequence of RGTTASSDTAITLIPRNALTAIVANKP (SEQ ID NO: 6), or a biologically active fragment from a reactive center loop of Serp-1, wherein the biologically active fragment comprises an amino acid sequence selected from the group consisting of IPRNAL (SEQ ID NO: 2), RNAL (SEQ ID NO: 3), TAIVANKPF (SEQ ID NO: 4), and GTTASSDTAITLIPR (SEQ ID NO: 5); and a chitosan-collagen hydrogel containing 1 μg of the Serp-1 polypeptide or the biologically active fragment from a reactive center loop of Serp-1 per 10 μL of the chitosan-collagen hydrogel.

2. The topical formulation of claim 1, further comprising one or more additional active ingredients.

3. The topical formulation of claim 2, wherein the one or more additional active ingredients comprises an antibiotic.

4. The topical formulation of claim 1, wherein the Serp-1 polypeptide further comprises an amino sequence with 90% sequence identity to residues 1-303 of SEQ ID NO: 1 and an amino sequence with 90% sequence identity to residues 331-350 of SEQ ID NO: 1.

5. The topical formulation of claim 1, wherein the chitosan-collagen hydrogel comprises an interconnected open porous structure.

6. The topical formulation of claim 1, wherein the Serp-1 polypeptide is metastable for at least four days.

7. The topical formulation of claim 1, wherein the chitosan-collagen hydrogel releases at least 75% of the Serp-1 polypeptide after four days.

8. A wound dressing, comprising:

an effective amount of a Serp-1 polypeptide, wherein the Serp-1 polypeptide comprises a reactive center loop comprising an amino acid sequence of RGTTASSDTAITLIPRNALTAIVANKP (SEQ ID NO: 6), or a biologically active fragment from a reactive center loop of Serp-1, wherein the biologically active fragment comprises an amino acid sequence selected from the group consisting of IPRNAL (SEQ ID NO: 2), RNAL (SEQ ID NO: 3), TAIVANKPF (SEQ ID NO: 4), and GTTASSDTAITLIPR SEQ ID NO: 5); and a chitosan-collagen hydrogel containing 1 μg of the Serp-1 polypeptide or the biologically active fragment from a reactive center loop of Serp-1 per 10 μL of the chitosan-collagen hydrogel.

9. The wound dressing of claim 8, further comprising one or more additional active ingredients.

10. The wound dressing of claim 9, wherein the one or more additional active ingredients comprises an antibiotic.

11. A kit for treating a wound in a subject, comprising the topical formulation of claim 1 and instructions for use.

12. A method of treating a wound in a subject in need thereof, comprising topically administering the topical formulation of claim 1 to the wound in the subject.

* * * * *